United States Patent [19]
Baszczynski et al.

[11] Patent Number: 5,756,324
[45] Date of Patent: May 26, 1998

[54] USE OF A MICROSPORE-SPECIFIC REGULATORY ELEMENT FOR PRODUCTION OF VIRUS AND INSECT-RESISTANT PLANTS

[75] Inventors: Chris Baszczynski, Urbandale; Eric Barbour, Des Moines, both of Iowa; Brian Miki; Jiro Hattori, both of Ottawa, Canada

[73] Assignee: Pioneer Hi-Bred International, Inc., Des Moines, Iowa

[21] Appl. No.: 625,198

[22] Filed: Apr. 1, 1996

Related U.S. Application Data

[62] Division of Ser. No. 345,756, Nov. 22, 1994, Pat. No. 5,633,438.

[51] Int. Cl.$^6$ .......................... C12N 15/29; C12N 15/32; C12N 15/33; C12N 15/82
[52] U.S. Cl. .................. 435/172.3; 435/69.1; 435/320.1; 435/418; 435/419; 536/23.6; 536/24.5; 536/23.71; 536/23.72; 800/205
[58] Field of Search ........................... 435/69.1, 172.3, 435/320.1, 418, 419; 536/23.6, 24.5, 23.71, 23.72; 800/205

[56] References Cited

PUBLICATIONS

Albani et al., "Characterization of a Pollen–Specific Gene Family . . . " *Plant Mol. Biol.*, 15:605–22, 1990.
Albani et al., "A Gene Showing Sequence Similarity to Pectin . . . ", *Plant Mol. Biol.*, 16:501–13, 1991.
Albani et al., "A Brassica Napus Gene Family Which Shows Sequence . . . ", *Plant Jrnl.*, 2:3;331–42, 1992.
Dzelzkalns et al., "Distinct cis—Acting Elements Direct Pistill–Specific . . . " *Plant Cell*, 5:855–63, 1993.
Guerrero et al., "Promoter Sequences From a Maize Pollen–Specific . . . ", *Mol. Gen. Genet*, 224:161–68, 1990.
Hamilton et al., "Dissection of a Pollen–Specific Promoter . . . ", *Plant Mol. Biol.*, 18:211–18, 1992.
Mariani et al., "A Chimaeric Ribonuclease–Inhibitor Gene . . . ", *Nature*, 357:384–87, 1992.
Mariani et al., "Induction of Male Sterility in Plants . . . ", *Nature*, 347:737–41, 1990.
McCormick et al., "Anther–Specific Genes: Molecular Characterization . . . ", *Plant Reprod.*, 1:128–35, 1989.
McCormick et al., "Molecular Analysis of Male Gametogenesis in Plants", *Trends Genet*, 7:9;298–303, 1991.
Spena et al., "Anther–Specific Expression of the rolB Gene . . . ", *Theor. Appl. Genet*, 84:520–27, 1992.
Thorsness et al., "A Brassica S–Locus Gene Promoter Targets Toxic . . . ", *Dev. Biol.*, 143:173–84, 1991.
Twell et al., "Promoter Analysis of Genes that are Coordinately . . . ", *Genes & Dev.*, 5:496–507, 1991.
Twell et al., "Pollen–Specific Gene Expression in Transgenic Plants . . . ", *Development*, 109:705–13, 1990.
Twell et al., "Isolation and Expression of Anther–Specific . . . ", *Mol. Gene Genet*, 217:240–45, 1989.
Van Tunen et al., "Pollen— and Anther–Specific chi Promoters from Petunia . . . ", *Plant Cell*, 2:393–401, 1990.
Leede-Plegt et al., "Induction and Differential Use of Various Promoters . . . ", *Plant Cell Rpts.*, 11:20–24, 1992.
Van Tunen et al., "Regulation of Chalcone Flavanone Isomerase (CHI) Gene . . . ", *Plant Miol. Biol.*, 12:539–51, 1989.
Vogt et al., "Pollination— or Wound–Induced Kaempferol Accumulation . . . ", *Plant Cell*, 6:11–23, 1994.
Weterings et al., "Characterization of a Pollen–Specific cDNA Clone . . . ", *Plant Mol. Biol.*, 18:1101–11, 1992.
Wing et al., "Molecular and Genetic Characterization of Two Pollen . . . ", *Plant Mol. Biol.*, 14:17–28, 1989.
Evans et al., "The Effects of Bibozymes on Gene Expression in Plants", *Biochem. Soc., Trans.*, vol. 20:3455, 1992.
Van Der Meer et al., "Antisense Inhibition of Flavonoid Biosynthesis in Petunia Anthers Results in Male Sterility", *The Plant Cell*, vol. 4:253–262, (1992).
Haseloff et al., "Simple RNA Enzymes With New and Highly Specific Endoribonuclease Activities", *Nature*, vol. 334:585–591, (1988).
Mo et al., "Biochemical Complementation of Chalcone Synthase Mutants Defines A Role for Flavonols in Functional Pollen", *Proc. Natl. Acad. Sci. USA*, vol. 89:7213–7217, (1992).
Koziel et al. 1993, Bio/Technology 11(2):194–200.
Abel et al. 1986, Science 232:738–743.

*Primary Examiner*—David T. Fox

[57] ABSTRACT

A novel DNA regulatory element that confers microspore-specific gene expression has been discovered, isolated, and characterized. The microspore-specific regulatory element can be used to control the expression of a foreign gene that disrupts the function of microspores. Thus, the control of pollen production can be achieved by using the microspore-specific regulatory element to produce male-sterile plants. Various methods can be used to restore male fertility in the F1 generation of such male-sterile plants. In addition, the microspore-specific regulatory element can be used to confer resistance to viral and insect pests.

8 Claims, 8 Drawing Sheets

FIG. 1A

```
ACAAAACTTCCGACGCAAAGAAA ATG GCA ACG TTC TCA GTT CTG TCT ACC TTC GCC GCG GCG
                         Met Ala Thr Phe Ser Val Leu Ser Thr Phe Ala Ala Ala

GCA ATT ACG TTG CAA CTA CTC CTA GTT CCA GCT TCA GCC TCT CCT CAC ATG AAA TAC
Ala Ile Thr Leu Gln Leu Leu Leu Val Pro Ala Ser Ala Ser Pro His Met Lys Tyr

GCT ATC TGC GAT CGC TCC CAC GAC CAA GAT TAC TGC GTT AAA ACA TTG ACC ATT GAC
Ala Ile Cys Asp Arg Ser His Asp Gln Asp Tyr Cys Val Lys Thr Leu Thr Ile Asp

ACC AAC CCC CCT ACA GCT GCT CCC ATT GGC CTG AAT CCA CTG GCC GAG GTG ATG GCG
Thr Asn Pro Pro Thr Ala Ala Pro Ile Gly Leu Asn Pro Leu Ala Glu Val Met Ala

CTC ACC ATA GCC CAC GCC GAG AAG ACA GCG GCT TTC GTG GCT GAG ACG GGT AAG GCT
Leu Thr Ile Ala His Ala Glu Lys Thr Ala Ala Phe Val Ala Glu Thr Gly Lys Ala

GAT CAA ACG TTT ACT GAG TAC CAC AAG GCC TAC TTA GCC GTG GTG GCT GAT CTC AAG
Asp Gln Thr Phe Thr Glu Tyr His Lys Ala Tyr Leu Ala Val Val Ala Asp Leu Lys
```

FIG. 1B

```
350                                                              375                                           400
AGC GCA AAC CTG AAG CTC AAG CAA TCC CCT GAC ACT GCT CAC TAC GAC GTT AGG TCT
Ser Ala Asn Leu Lys Leu Lys Gln Ser Pro Asp Thr Ala His Tyr Asp Val Arg Ser 425                                                              450
TCG ACC GAC CAG ATG AAG CGC GTG GAG GGA TTA GTT GCC AGC AAA AAT GAC CAG GCT
Ser Thr Asp Gln Met Lys Arg Val Glu Gly Leu Val Ala Ser Lys Asn Asp Gln Ala 475                                                              500
TCA ACT ACT CTT AAG GAA ATG ACG GTG CAG ATG GAG AAA CTT CTT GAT CTT GCA GCT
Ser Thr Thr Leu Lys Glu Met Thr Val Gln Met Glu Lys Leu Leu Asp Leu Ala Ala 525                                                              550
AGT GCC GCC GAT GCT GTG GAC GAT GAT GAC GAT GAG AAC ATC CAC CGT CGC GTC TGA TTT
Ser Ala Ala Asp Ala Val Asp Asp Asp Asp Glu Asn Ile His Arg Arg Val ***

600                                                                                  625                                              650
TAAACCGGTCCGGTTTCGTTTTTT GTGTTCACAATACAAAATATAATAA ATAAATGAATATACATATACACACA 675                                                              700                                              725
CACAAATGTGTTGTGATAAACTAGT AATTAAGTTTTTGAAATATTTGCAG AACTAAATGTTGTCAATATTTTTGGC 750                                                              775
ATATATAAAGAGTCTGCTGTATTAT CTTTTTATAAAACTAAATATAAATC TGATTTGTATC
```

FIG. 2A

```
  1  GCACCGCATC AAAGTGATGC GGAAGGAGTA ATTATTCTGT AAATTTAAAT ATTTAGTCTT ACATTGTTCA
 71  AATTTTTATG TTTTATATTA TTTTATTTTT TGATTTTGAC GATTTAAGTA TATTTGAATT TTTTTAAGAA
141  AAATACATAA TTAAAATGGG TACCCGAACT CGAATCTGAA TCGAACCCAC AATGATTCGA ACAAAATTCA
211  AACCAAAATT TATAAATATT CCAATATACGAT TGAATTTCT AATATAAGAA TCAGAAATCT GAATAGATTA
281  ACTGAATTCA AACAGTATA AGAGTGTCCA CCCCAACAAA TCCCTTAGTA CAATATATAG TTATAAATAA
351  TTCAATAAAC TATTTCATTA TGCACAGCGC GGACTACTAC TAGTATAGTA TAATGTATGT CAAATAAAAC
421  TTCAGTGAAA TGTGTTCATA TTAGATTAGA CCACTTCTTT TCTATGATCA CCAAGGACCT CAACACTGT
491  CACGACATAG CTCAATTTTC TAAACAAAGA AAGAAGATCA CAGACGATTT TTTCGTTGAC TAAATCTATA
561  CAAACCACAT ACTATTAGA TAGGTTCTCC AAATTTAGCA AATATAAGCA AACTTTTAGT AAAAACCTTA
631  CGCATTTTAC ATCAATTCTT AATATAGTAG TTTCCAAGAA TATCAAACGT CCCTGACCAA GCCCTAGGTG
701  TACTTGTATA TATACCCACC CACAAACTAA AAGCAAATCA ACATACAGAA AACTGAATAA CAACCGGAAG
771  AAAAAGAGA AAAAAATAAA TAAAACAAAA CTTCCGACGC AAAGAAAATG GCAACGTTCT CAGTTCTGTC
841  TACCTTCGCC GCGGCGGCAA TTACGTTGCA ACTACTCCTA GTTCCAGCTT CAGCCTCTCC TCACATGAAA
911  TACATTGACG TCGCTCCCAC GACCAAGATT ACTGCGTAA AACATTGACC ACCAACCCCC
```

FIG. 2B

```
 981 CTACAGCTGC TCCATTGGC CTGGTACTCA TCTTTAAACC ACTGTCTCTT TGTTTGCGTT AAATCACAGA
1051 AGAAATTTAC GTTTGAATTA TGGTTTATTC AGTTTATTTG GCAGTCCGGT AATATGTAAT CCGAAAATCT
1121 TCTAACATTA GTCGAAAAAC ATTTTAAACA GACAATCCGA CAATGTGATA CTTTTTTCCA CACTGTAGCA
1191 TCTAGTGTGT TTATACCGCA GCTGGCCGGA TTAGCTAGCT GCATATATAT TAAAAAAAAA TCATGTTTAC
1261 TTAATATGTT TCAAAAAATAC AACTGCATAT GCTTTACGTG TGAAAGAGCT TAAACGAGAA TGATCATTAG
1331 TATTAATACT AATAAAATCT CTTTATTATC TCTAGAATCC ACTGGCCGAG GTGATGGCGC TCACCATAGC
1401 CCACGCCGAG AAGACAGCGG CTTTCGTGGC TGAGACGGGT AAGGCTGATC AAACGTTTAC TGAGTACCAC
1471 AAGGCCTACT TAGCCGTGGT GGCTGATCTC AAGAGGCGCAA ACCTGAAGCT CAAGCAATCC CCTGACACTG
1541 CTCACTACGA CGTTAGGTCT TCGACCGACC AGATGAAGCG CGTGGAGGGA TTAGTTGCCA GCAAAATGA
1611 CCAGGCTTCA ACTACTCTTA AGGAAATGAC GGTGCAGATG GAGAAACTTC TTGATCTTGC AGCTAGTGCC
1681 GCCGATGCTG TGGACGACGA TGATGAGAAC ATCCACCGTC GCGTCTGATT TTAAACCGGT CCGGTTTCGT
1751 TTTTTGTGT TCACAATACA AAATATAATA AATAAATGAA TATACATATA CACACACACA AATGTGTTGT
          ***                       **********
1821 GATAAACTAG TAATTAAGTT TTTGAAATAT TTGCAGAACT AATGTTGTCA ATATTTTGG CATATATAAA
1891 GAGTCTGCTG TATTATCTTT TTATAAAACT AAATATAAAT CTGATTTGTA TCAATTGTTG GACAACCCAA
1961 AAGCGCCAAG ACATCACCTG GTACAAACAT ATTGACTTTT GTAAGCTTAT CGATACCGTC GACCTCGA
```

FIG. 3A

```
  1  GGCCGTCGAC GCATCAAAGT GATGCGGAAG GAGTAATTAT TCTGTAAATT
        SalI
 51  TAAATATTTA GTCTTACATT GTTCAAATTT TTATGTTTTA TATTATTTTA
101  TTTTTGATT TTGACGATTT AAGTATATTT GAATTTTTT AAGAAAAATA
151  CATAATTAAA ATGGGTACCC GAACTCGAAT CTGAATCGAA CCCACAATGA
201  TTCGAACAAA ATTCAAACCA AAATTATAA ATATTCCAAT ACGATTGAAT
251  TTTCTAATAT AAGAATCAGA AATCTGAATA GATTAACTGA ATTCAAACAG
301  GTATAAGAGT GTCCACCCCA ACAAATCCCT TAGTACAATA TATAGTTATA
351  AATAATTCAA TAAACTATTT CATTATGCAC AGCGCGGACT ACTACTAGTA
401  TAGTATAATG TATGTCAAAT AAAACTTCAG TGAAATGTGT TCATATTAGA
```

FIG. 3B

```
451  TTAGACCACT TCTTTTCTAT GATCACCAAG GACCTCAACA CTTGTCACGA
501  CATAGCTCAA TTTCTAAAC  AAAGAAAGAA GATCACAGAC GATTTTTCG
551  TTGACTAAAT CTATACAAAC CACATACTAT TTAGATAGGT TCTCCAAATT
601  TAGCAAATAT AAGCAAACTT TTAGTAAAAA CCTTACGCAT TTTACATCAA
651  TTCTTAATAT AGTAGTTTCC AAGAATATCA AACGTCCCTG ACCAAGCCCT
701  AGGTGTACTT GTATATATAC CCACCCACAA ACTAAAAGCA AATCAACATA
751  CAGAAAACTG AATAACAACC GGAAGAAAAA AGAGAAAAAA ATAAATAAAA
801  CAAAACTTCC GACGCAAAGA CCATGGCAAC GTTCTAGACC CGGG
                                    ───────    ─────────
                                      NcoI        XbaI
```

DP5476
MSp = B. NAPUS MICROSPORE SPECIFIC PROMOTER

DP5477
MSP = B NAPUS MICROSPORE SPECIFIC PROMOTER

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 786 base pairs
        ( B ) TYPE: nucleic acid
        ( C ) STRANDEDNESS: single
        ( D ) TOPOLOGY: linear -continued (i i) MOLECULE TYPE: DNA (genomic)

(i x) FEATURE:
    (A) NAME/KEY: CDS
    (B) LOCATION: 24..569

(x i) SEQUENCE DESCRIPTION: SEQ ID NO:1:

```
ACAAAACTTC CGACGCAAAG AAA ATG GCA ACG TTC TCA GTT CTG TCT ACC           50
                         Met Ala Thr Phe Ser Val Leu Ser Thr
                          1               5

TTC GCC GCG GCG GCA ATT ACG TTG CAA CTA CTC CTA GTT CCA GCT TCA         98
Phe Ala Ala Ala Ala Ile Thr Leu Gln Leu Leu Leu Val Pro Ala Ser
 10              15                  20                      25

GCC TCT CCT CAC ATG AAA TAC ATT GAC GCT ATC TGC GAT CGC TCC CAC        146
Ala Ser Pro His Met Lys Tyr Ile Asp Ala Ile Cys Asp Arg Ser His
                 30                  35                  40

GAC CAA GAT TAC TGC GTT AAA ACA TTG ACC ACC AAC CCC CCT ACA GCT        194
Asp Gln Asp Tyr Cys Val Lys Thr Leu Thr Thr Asn Pro Pro Thr Ala
             45                  50                  55

GCT CCC ATT GGC CTG AAT CCA CTG GCC GAG GTG ATG GCG CTC ACC ATA        242
Ala Pro Ile Gly Leu Asn Pro Leu Ala Glu Val Met Ala Leu Thr Ile
         60                  65                  70

GCC CAC GCC GAG AAG ACA GCG GCT TTC GTG GCT GAG ACG GGT AAG GCT        290
Ala His Ala Glu Lys Thr Ala Ala Phe Val Ala Glu Thr Gly Lys Ala
     75                  80                  85

GAT CAA ACG TTT ACT GAG TAC CAC AAG GCC TAC TTA GCC GTG GTG GCT        338
Asp Gln Thr Phe Thr Glu Tyr His Lys Ala Tyr Leu Ala Val Val Ala
 90                  95                 100                 105

GAT CTC AAG AGC GCA AAC CTG AAG CTC AAG CAA TCC CCT GAC ACT GCT        386
Asp Leu Lys Ser Ala Asn Leu Lys Leu Lys Gln Ser Pro Asp Thr Ala
                 110                 115                 120

CAC TAC GAC GTT AGG TCT TCG ACC GAC CAG ATG AAG CGC GTG GAG GGA        434
His Tyr Asp Val Arg Ser Ser Thr Asp Gln Met Lys Arg Val Glu Gly
             125                 130                 135

TTA GTT GCC AGC AAA AAT GAC CAG GCT TCA ACT ACT CTT AAG GAA ATG        482
Leu Val Ala Ser Lys Asn Asp Gln Ala Ser Thr Thr Leu Lys Glu Met
         140                 145                 150

ACG GTG CAG ATG GAG AAA CTT CTT GAT CTT GCA GCT AGT GCC GCC GAT        530
Thr Val Gln Met Glu Lys Leu Leu Asp Leu Ala Ala Ser Ala Ala Asp
     155                 160                 165

GCT GTG GAC GAC GAT GAT GAG AAC ATC CAC CGT CGC GTC TGATTTAAA          579
Ala Val Asp Asp Asp Asp Glu Asn Ile His Arg Arg Val
 170                 175                 180

CCGGTCCGGT TTCGTTTTTT TGTGTTCACA ATACAAAATA TAATAAATAA ATGAATATAC      639

ATATACACAC ACACAAATGT GTTGTGATAA ACTAGTAATT AAGTTTTTGA AATATTTGCA      699

GAACTAATGT TGTCAATATT TTTGGCATAT ATAAAGAGTC TGCTGTATTA TCTTTTTATA      759

AAACTAAATA TAAATCTGAT TTGTATC                                          786
```

(2) INFORMATION FOR SEQ ID NO:2:

(i) SEQUENCE CHARACTERISTICS:
        (A) LENGTH: 182 amino acids
        (B) TYPE: amino acid
        (D) TOPOLOGY: linear (i i) MOLECULE TYPE: protein (x i) SEQUENCE DESCRIPTION: SEQ ID NO:2:

```
Met Ala Thr Phe Ser Val Leu Ser Thr Phe Ala Ala Ala Ala Ile Thr
 1               5                  10                      15

Leu Gln Leu Leu Leu Val Pro Ala Ser Ala Ser Pro His Met Lys Tyr
```

|  | | | | | 20 | | | | | 25 | | | | | 30 | |
|---|---|---|---|---|---|---|---|---|---|---|---|---|---|---|---|---|

Ile Asp Ala Ile Cys Asp Arg Ser His Asp Gln Asp Tyr Cys Val Lys
            35                    40                    45

Thr Leu Thr Thr Asn Pro Pro Thr Ala Ala Pro Ile Gly Leu Asn Pro
    50                  55                  60

Leu Ala Glu Val Met Ala Leu Thr Ile Ala His Ala Glu Lys Thr Ala
65                  70                  75                  80

Ala Phe Val Ala Glu Thr Gly Lys Ala Asp Gln Thr Phe Thr Glu Tyr
                85                  90                  95

His Lys Ala Tyr Leu Ala Val Val Ala Asp Leu Lys Ser Ala Asn Leu
            100                 105                 110

Lys Leu Lys Gln Ser Pro Asp Thr Ala His Tyr Asp Val Arg Ser Ser
        115                 120                 125

Thr Asp Gln Met Lys Arg Val Glu Gly Leu Val Ala Ser Lys Asn Asp
    130                 135                 140

Gln Ala Ser Thr Thr Leu Lys Glu Met Thr Val Gln Met Glu Lys Leu
145                 150                 155                 160

Leu Asp Leu Ala Ala Ser Ala Ala Asp Ala Val Asp Asp Asp Asp Glu
                165                 170                 175

Asn Ile His Arg Arg Val
            180

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

GGCCGAATTC GCCGCCGCGG CGAAGGTAGA                                          30

(2) INFORMATION FOR SEQ ID NO:4:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

GGCCGAATTC CTGCCTTACC CGTCTCAGCC ACG                                    33

(2) INFORMATION FOR SEQ ID NO:5:

(i) SEQUENCE CHARACTERISTICS:
        (A) LENGTH: 2039 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GCCAGGGTTC CGCACCGCAT CAAAGTGATG CGGAAGGAGT AATTATTCTG TAAATTTAAA    60

TATTTAGTCT TACATTGTTC AAATTTTTAT GTTTATATT ATTTTATTTT TTGATTTTGA    120

CGATTTAAGT ATATTGAAT TTTTTAAGA AAAATACATA ATTAAAATGG GTACCCGAAC    180

```
TCGAATCTGA ATCGAACCCA CAATGATTCG AACAAAATTC AAACCAAAAT TTATAAATAT      240
TCCAATACGA TTGAATTTTC TAATATAAGA ATCAGAAATC TGAATAGATT AACTGAATTC      300
AAACAGGTAT AAGAGTGTCC ACCCCAACAA ATCCCTTAGT ACAATATATA GTTATAAATA      360
ATTCAATAAA CTATTTCATT ATGCACAGCG CGGACTACTA CTAGTATAGT ATAATGTATG      420
TCAAATAAAA CTTCAGTGAA ATGTGTTCAT ATTAGATTAG ACCACTTCTT TTCTATGATC      480
ACCAAGGACC TCAACACTTG TCACGACATA GCTCAATTTT CTAAACAAAG AAAGAAGATC      540
ACAGACGATT TTTTCGTTGA CTAAATCTAT ACAAACCACA TACTATTTAG ATAGGTTCTC      600
CAAATTTAGC AAATATAAGC AAACTTTTAG TAAAAACCTT ACGCATTTTA CATCAATTCT      660
TAATATAGTA GTTTCCAAGA ATATCAAACG TCCCTGACCA AGCCCTAGGT GTACTTGTAT      720
ATATACCCAC CCACAAACTA AAAGCAAATC AACATACAGA AAACTGAATA ACAACCGGAA      780
GAAAAAGAG AAAAAAATAA ATAAACAAA ACTTCCGACG CAAAGAAAAT GGCAACGTTC        840
TCAGTTCTGT CTACCTTCGC CGCGGCGGCA ATTACGTTGC AACTACTCCT AGTTCCAGCT     900
TCAGCCTCTC CTCACATGAA ATACATTGAC GCTATCTGCG ATCGCTCCCA CGACCAAGAT     960
TACTGCGTTA AAACATTGAC CACCAACCCC CCTACAGCTG CTCCCATTGG CCTGGTACTC    1020
ATCTTTAAAC CACTGTCTCT TTGTTTGCGT TAAATCACAG AAGAAATTTA CGTTTGAATT    1080
ATGGTTTATT CAGTTTATTT GGCAGTCCGG TAATATGTAA TCCGAAAATC TTCTAACATT    1140
AGTCGAAAAA CATTTTAAAC AGACAATCCG ACAATGTGAT ACTTTTTCC ACACTGTAGC     1200
ATCTAGTGTG TTTATACCGC AGCTGGCCGG ATTAGCTAGC TGCATATATA TTAAAAAAAA    1260
ATCATGTTTA CTTAATATGT TTCAAAAATA CAACTGCATA TGCTTTACGT GTGAAAGAGC    1320
TTAAACGAGA ATGATCATTA GTATTAATAC TAATAAAATC TCTTTATTAT CTCTAGAATC    1380
CACTGGCCGA GGTGATGGCG CTCACCATAG CCCACGCCGA GAAGACAGCG GCTTTCGTGG    1440
CTGAGACGGG TAAGGCTGAT CAAACGTTTA CTGAGTACCA CAAGGCCTAC TTAGCCGTGG    1500
TGGCTGATCT CAAGAGCGCA AACCTGAAGC TCAAGCAATC CCCTGACACT GCTCACTACG    1560
ACGTTAGGTC TTCGACCGAC CAGATGAAGC GCGTGGAGGG ATTAGTTGCC AGCAAAAATG    1620
ACCAGGCTTC AACTACTCTT AAGGAAATGA CGGTGCAGAT GGAGAAACTT CTTGATCTTG    1680
CAGCTAGTGC CGCCGATGCT GTGGACGACG ATGATGAGAA CATCCACCGT CGCGTCTGAT    1740
TTTAAACCGG TCCGGTTTCG TTTTTTTGTG TTCACAATAC AAAATATAAT AAATAAATGA    1800
ATATACATAT ACACACACAC AAATGTGTTG TGATAAACTA GTAATTAAGT TTTTGAAATA    1860
TTTGCAGAAC TAATGTTGTC AATATTTTG GCATATATAA AGAGTCTGCT GTATTATCTT     1920
TTTATAAAAC TAAATATAAA TCTGATTTGT ATCAATTGTT GGACAACCCA AAAGCGCCAA    1980
GACATCACCT GGTACAAACA TATTGACTTT TGTAAGCTTA TCGATACCGT CGACCTCGA     2039
```

( 2 ) INFORMATION FOR SEQ ID NO:6:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

GGCCGTCGAC GCATCAAAGT GATGCGGAAG GAG                                                     33

( 2 ) INFORMATION FOR SEQ ID NO:7:

```
        ( i ) SEQUENCE CHARACTERISTICS:
                ( A ) LENGTH: 35 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:7:

CCCGGGTCTA  GAACGTTGCC  ATGGTCTTTG  CGTCG                                           3 5

( 2 ) INFORMATION FOR SEQ ID NO:8:

( i ) SEQUENCE CHARACTERISTICS:
                ( A ) LENGTH: 859 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:8:

CATAGTCGAT  CTTAGGGCCG  TCGACGCATC  AAAGTGATGC  GGAAGGAGTA  ATTATTCTGT              6 0

AAATTTAAAT  ATTTAGTCTT  ACATTGTTCA  AATTTTTATG  TTTTATATTA  TTTTATTTTT              1 2 0

TGATTTTGAC  GATTTAAGTA  TATTTGAATT  TTTTTAAGAA  AAATACATAA  TTAAAATGGG              1 8 0

TACCCGAACT  CGAATCTGAA  TCGAACCCAC  AATGATTCGA  ACAAAATTCA  AACCAAAATT              2 4 0

TATAAATATT  CCAATACGAT  TGAATTTTCT  AATATAAGAA  TCAGAAATCT  GAATAGATTA              3 0 0

ACTGAATTCA  AACAGGTATA  AGAGTGTCCA  CCCCAACAAA  TCCCTTAGTA  CAATATATAG              3 6 0

TTATAAATAA  TTCAATAAAC  TATTTCATTA  TGCACAGCGC  GGACTACTAC  TAGTATAGTA              4 2 0

TAATGTATGT  CAAATAAAAC  TTCAGTGAAA  TGTGTTCATA  TTAGATTAGA  CCACTTCTTT              4 8 0

TCTATGATCA  CCAAGGACCT  CAACACTTGT  CACGACATAG  CTCAATTTTC  TAAACAAAGA              5 4 0

AAGAAGATCA  CAGACGATTT  TTTCGTTGAC  TAAATCTATA  CAAACCACAT  ACTATTTAGA              6 0 0

TAGGTTCTCC  AAATTTAGCA  AATATAAGCA  AACTTTTAGT  AAAAACCTTA  CGCATTTTAC              6 6 0

ATCAATTCTT  AATATAGTAG  TTTCCAAGAA  TATCAAACGT  CCCTGACCAA  GCCCTAGGTG              7 2 0

TACTTGTATA  TATACCCACC  CACAAACTAA  AAGCAAATCA  ACATACAGAA  AACTGAATAA              7 8 0

CAACCGGAAG  AAAAAGAGA   AAAAAATAAA  TAAAACAAAA  CTTCCGACGC  AAAGACCATG              8 4 0

GCAACGTTCT  AGACCCGGG                                                               8 5 9
```

USE OF A MICROSPORE-SPECIFIC REGULATORY ELEMENT FOR PRODUCTION OF VIRUS AND INSECT-RESISTANT PLANTS

CROSS-REFERENCE TO RELATED APPLICATIONS

This application is a divisional application of application U.S. Ser. No. 08/345,756, filed Nov. 22, 1994, now U.S. Pat. No. 5,633,438.

BACKGROUND OF THE INVENTION

1. Field of the Invention

The present invention relates to a novel regulatory element which confers microspore-specificity to gene expression. In particular, this invention is directed to a microspore-specific regulatory element of the Brassica napus Bnm1 gene, and to using such a regulatory element to produce transgenic, male-sterile plants. This invention also is directed to a method for restoring male fertility in the progeny of male-sterile plants. Moreover, the present invention relates to the use of a microspore-specific regulatory element to protect against viral and insect pests.

2. Background

Control of pollen fertility is essential in hybrid crop production. Traditional methods for regulating pollen fertility include manual emasculation of plants to be used as the female parent and application of chemical compositions. According to the latter method, hybrid seeds are produced by the cross fertilization of chemically-treated female plants with pollen from non-treated plants. Both approaches, however, are labor-intensive. Moreover, it is preferable to avoid the introduction of toxic chemicals into the environment.

Another approach to the control of fertility is based upon the use of a cytoplasmic gene(s) for male sterility. The problem with this approach is that the expression of certain cytoplasmic male sterility genes is accompanied by an increased susceptibility to fungal pathogens. For example, the extensive use of the cmsT cytotype in maize led to an epiphytic outbreak of Southern Corn Leaf Blight in the early 1970's. Although additional cytoplasmic male sterility cytotypes have become available, their use has not become widespread due to the concern over possible susceptibility to pathogens.

The ability to produce hybrid lines has particular economic importance for oil seed crops. For example, Brassica napus $F_1$, hybrid lines typically produce yields that are greater than 20 to 70%, compared with established lines. Thompson, *Adv. Appl. Biol.* 7: 1 (1983); Johnston, *Euphytica* 20: 81 (1971). The most economic and flexible approach to controlling fertility in Brassica utilizes a self-incompatibility system that is naturally present in Brassica species. Gowers, *Euphytica* 24: 537 (1975). However, the self-incompatibility system is not reliably effective under certain environmental conditions, such as elevated temperatures.

A need therefore exists for a method to control pollen production without reliance on naturally occurring male sterility or self-incompatibility genes or, the traditional manual and chemical methods.

SUMMARY OF THE INVENTION

Accordingly, it is an object of the present invention to provide a method to produce male-sterile plants using an expression vector that disrupts the function of microspores.

It is a further object of this invention to provide a DNA regulatory element that confers microspore-specific gene expression.

These and other objects are achieved, in accordance with one embodiment of the present invention by the provision of an isolated DNA molecule, wherein the DNA molecule comprises a nucleotide sequence selected from the group consisting of (a) SEQ ID NO: 8, (b) a nucleotide sequence that has substantial sequence similarity with SEQ ID NO: 8, and (c) a functional fragment of (a) or (b), wherein the DNA molecule is a microspore-specific regulatory element.

The present invention also contemplates expression vectors comprising a microspore-specific regulatory element. Such expression vectors may further comprise a promoter, wherein the function of the promoter is under the control of a microspore-specific regulatory element. Examples of suitable promoters include a Bnm1 promoter, an anther-specific promoter and the CaMV 35S core promoter.

The present invention also is directed to an expression vector further comprising a foreign gene which is operably linked to a promoter, wherein the product of the foreign gene disrupts the function of microspores.

The present invention further contemplates a method of using such expression vectors to produce a male-sterile plant, comprising the step of introducing an expression vector into embryogenic plant cells, wherein the foreign gene is selected from the group consisting of a structural gene, an antisense gene, a ribozyme gene and an external guide sequence gene. For example, an expression vector may be introduced into embryogenic plant cells of *Brassica napus*.

Suitable structural genes encode a protein selected from the group consisting of diphtheria toxin, pokeweed antiviral protein, *Aspergillus oryzae* RNase-T1, barnase and the rolB gene product.

A suitable product of an antisense gene is selected from the group consisting of actin antisense RNA, tubulin antisense RNA, ubiquitin antisense RNA, ubiquitin conjugating enzyme antisense RNA, ubiquitin carrier protein antisense RNA, elongation factor antisense RNA and chalcone synthase antisense RNA.

Moreover, ribozyme genes or external guide sequence genes may comprise nucleotide sequences selected from the group consisting of actin nucleotide sequences, tubulin nucleotide sequences, ubiquitin nucleotide sequences, ubiquitin conjugating enzyme nucleotide sequences, ubiquitin carrier protein nucleotide sequences, elongation factor nucleotide sequences and chalcone synthase nucleotide sequences.

The present invention also is directed to a method of producing a male-sterile plant, comprising:

(a) constructing an expression vector comprising a microspore-specific regulatory element, a promoter, and a foreign gene, wherein the microspore-specific regulatory element comprises a nucleotide sequence selected from the group consisting of (i) SEQ ID NO: 8, (ii) a nucleotide sequence that has substantial sequence similarity with SEQ ID NO: 8, and (iii) fragments of (i) or (ii), wherein the microspore-specific regulatory element in conjunction with the promoter control the expression of the foreign gene, and wherein the product of the foreign gene disrupts the function of microspores, thereby producing a male-sterile plant.

Such a method may further comprise the step of (b) introducing the expression vector into embryogenic plant cells.

The present invention further contemplates a method of using a microspore-specific regulatory element to produce a male-fertile hybrid plant, comprising:

(a) producing a first parent male-sterile plant comprising an expression vector that comprises a microspore-specific regulatory element, a promoter, and a first foreign gene, wherein the microspore-specific regulatory element in conjunction with the promoter control the expression of the first foreign gene, and wherein the product of the first foreign gene disrupts the function of microspores;

(b) producing a second parent plant comprising an expression vector that comprises the microspore-specific regulatory element, a promoter and a second foreign gene, wherein the microspore-specific regulatory element in conjunction with the promoter control the expression of the second foreign gene; and (c) cross-fertilizing the first parent with the second parent to produce a hybrid plant, wherein the microspores of the hybrid plant express the second foreign gene, and wherein the product of the second foreign gene prevents the disruption of microspore function by the product of the first foreign gene, thereby producing a male-fertile hybrid plant.

For example, the first foreign gene can encode barnase and the second foreign gene can encode a barnase inhibitor. Alternatively, the product of the first foreign gene can be diphtheria toxin and the product of the second foreign gene can be diphtheria toxin ribozyme.

The present invention also is directed to a method for restoring fertility of a male-sterile hybrid plant, comprising treating the male-sterile hybrid plant with flavonol aglycone, wherein the male-sterile plant comprises an expression vector comprising (i) a microspore-specific regulatory element, (ii) a promoter, and (iii) a foreign gene, wherein the microspore-specific regulatory element in conjunction with the promoter control the expression of the foreign gene, and wherein the foreign gene expresses chalcone synthase antisense RNA, thereby producing flavonol-deficient microspores. Kaempferol is an example of a suitable flavonol aglycone.

The present invention is further directed to a method for producing transgenic plants resistant to disease caused by virus or insect, comprising constructing an expression vector comprising a microspore-specific regulatory element, a promoter, and a foreign gene, wherein the microspore-specific regulatory element comprises a nucleotide sequence selected from the group consisting of (i) SEQ ID NO: 8, (ii) a nucleotide sequence that has substantial sequence similarity with SEQ ID NO: 8, and (iii) fragments of (i) or (ii), wherein the microspore-specific regulatory element in conjunction with the promoter control the expression of the foreign gene, and wherein the product of the foreign gene disrupts the function of the virus or encodes an insecticidal toxin, thereby conferring disease resistance. The virus-disrupting foreign gene product may be selected from the group consisting of viral coat protein, 2'-5' oligoadenylate synthetase, viral genome antisense RNA and pokeweed antiviral protein, whereas a suitable insecticidal toxin is a *Bacillus thuringiensis* endotoxin.

BRIEF DESCRIPTION OF THE DRAWINGS

FIG. 1 presents the nucleotide sequence [SEQ ID NO: 1] of Bnm1 cDNA with its corresponding amino acid sequence [SEQ ID NO: 2]. The ATG start codon, TGA stop codon and a putative polyadenylation signal sequence are double underlined.

FIG. 2 presents the nucleotide sequence [SEQ ID NO: 5] of the Bnm1 genomic clone including promoter, coding region and a single intron (in italics). The underlined region is identical to the Bnm1 cDNA sequence. The ATG start codon, TGA stop codon and a putative polyadenylation signal sequence are indicated by asterisks.

FIG. 3 presents the nucleotide sequence [SEQ ID NO: 8] of the PCR-amplified promoter fragment used for cloning of the Bnm1 promoter. The ATG start codon is present within the NcoI restriction site.

DETAILED DESCRIPTION OF THE INVENTION

1. Definitions

Figure 4:
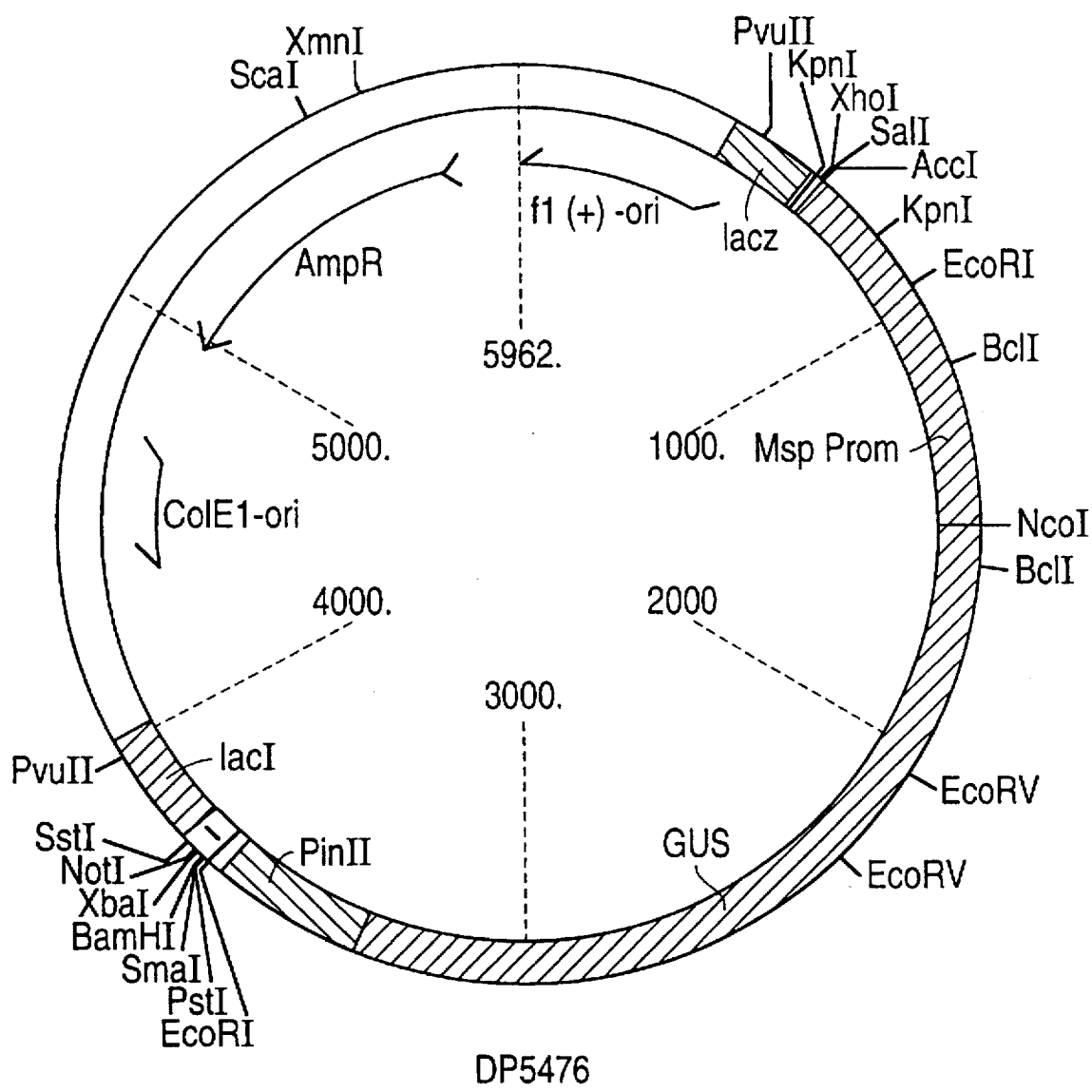
FIG. 4 presents a map of vector DP5476 which contains the *Brassica napus* microspore promoter (Msp Prom) driving the GUS gene-PINII terminator cassette inserted into the SalI-EcoRI sites of pBlueScript®II SK+. The vector also contains the ampicillin resistance gene (AmpR) as a selectable marker for *E. coli* transformations.

In the description that follows, a number of terms are used extensively. The following definitions are provided to facilitate understanding of the invention.

A structural gene is a DNA sequence that is transcribed into messenger RNA (mRNA) which is then translated into a sequence of amino acids characteristic of a specific polypeptide.

A promoter is a DNA sequence that directs the transcription of a structural gene. Typically, a promoter is located in the 5' region of a gene, proximal to the transcriptional start site of a structural gene. If a promoter is an inducible promoter, then the rate of transcription increases in response to an inducing agent. In contrast, the rate of transcription is not regulated by an inducing agent if the promoter is a constitutive promoter.

A core promoter contains essential nucleotide sequences for promoter function, including the TATA box and start of transcription. By this definition, a core promoter may or may not have detectable activity in the absence of specific sequences that may enhance the activity or confer tissue specific activity. For example, the Cauliflower Mosaic Virus (CaMV) 35S core promoter consists of about 33 nucleotides 5'-ward of the transcriptional start site of the 35S genome.

A microspore-specific regulatory element is a DNA sequence that directs a higher level of transcription of an associated gene in microspores than in some or all other tissues of a plant. For example, the Bnm1 gene, described herein, is expressed in microspores during the binucleate and trinucleate stages of development. The microspore-specific regulatory element of the Bnm1 gene can direct the expression of a foreign gene in microspores, but not in anther wall, pistil or sepal tissues.

An isolated DNA molecule is a fragment of DNA that is not integrated in the genomic DNA of an organism. For example, the microspore-specific regulatory element of the Bnm1 gene is a DNA fragment that has been separated from the genomic DNA of *Brassica napus*. Another example of an isolated DNA molecule is a chemically-synthesized DNA molecule that is not integrated in the genomic DNA of an organism.

An enhancer is a DNA regulatory element that can increase the efficiency of transcription, regardless of the distance or orientation of the enhancer relative to the start site of transcription.

Complementary DNA (cDNA) is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand.

The term expression refers to the biosynthesis of a gene product. For example, in the case of a structural gene, expression involves transcription of the structural gene into MRNA and the translation of mRNA into one or more polypeptides.

A cloning vector is a DNA molecule, such as a plasmid, cosmid, or bacteriophage, that has the capability of replicating autonomously in a host cell. Cloning vectors typically contain one or a small number of restriction endonuclease recognition sites at which foreign DNA sequences can be inserted in a determinable fashion without loss of an essential biological function of the vector, as well as a marker gene that is suitable for use in the identification and selection of cells transformed with the cloning vector. Marker genes typically include genes that provide tetracycline resistance or ampicillin resistance.

An expression vector is a DNA molecule comprising a gene that is expressed in a host cell. Typically, gene expression is placed under the control of certain regulatory elements, including constitutive or inducible promoters, tissue-specific regulatory elements, and enhancers. Such a gene is said to be "operably linked to" the regulatory elements.

A foreign gene refers in the present description to a DNA sequence that is operably linked to at least one heterologous regulatory element. For example, any gene other than the Bnm1 structural gene is considered to be a foreign gene if the expression of that gene is controlled by a microspore-specific regulatory element of the Bnm1 gene.

A recombinant host may be any prokaryotic or eukaryotic cell that contains either a cloning vector or expression vector. This term also includes those prokaryotic or eukaryotic cells that have been genetically engineered to contain the cloned gene(s) in the chromosome or genome of the host cell.

A transgenic plant is a plant having one or more plant cells that contain an expression vector.

In eukaryotes, RNA polymerase II catalyzes the transcription of a structural gene to produce mRNA. A DNA molecule can be designed to contain an RNA polymerase II template in which the RNA transcript has a sequence that is complementary to that of a specific mRNA. The RNA transcript is termed an antisense RNA and a DNA sequence that encodes the antisense RNA is termed an antisense gene. Antisense RNA molecules are capable of binding to mRNA molecules, resulting in an inhibition of mRNA translation.

A ribozyme is an RNA molecule that contains a catalytic center. The term includes RNA enzymes, self-splicing RNAs, and self-cleaving RNAs. A DNA sequence that encodes a ribozyme is termed a ribozyme gene.

An external guide sequence is an RNA molecule that directs the endogenous ribozyme, RNase P, to a particular species of intracellular mRNA, resulting in the cleavage of the mRNA by RNase P. A DNA sequence that encodes an external guide sequence is termed an external guide sequence gene.

Two nucleic acid molecules are considered to have a substantial sequence similarity if their nucleotide sequences share a similarity of at least 65%. Sequence similarity determinations can be performed, for example, using the FASTA program (Genetics Computer Group; Madison, Wis.). Alternatively, sequence similarity determinations can be performed using BLASTP (Basic Local Alignment Search Tool) of the Experimental GENIFO(R) BLAST Network Service. See Altschul et al., *J. Mol. Biol.* 215: 403 (1990). Also, see Pasternak et al., "Sequence Similarity Searches, Multiple Sequence Alignments, and Molecular Tree Building," in METHODS IN PLANT MOLECULAR BIOLOGY AND BIOTECHNOLOGY, Glick et al. (eds.), pages 251–267 (CRC Press 1993).

2. Overview

Microspore-specific genes are known in the art. See, for example, Wing et al., *Plant Molec. Biol.* 14: 17 (1989), Albani et al., *Plant Molec. Biol.* 15: 605 (1990), Guerrero et al., *Mol. Gen. Genet.* 224: 161 (1990), Twell et al., *Development* 109: 705 (1990), van Tunen et al., *The Plant Cell* 2: 393 (1990), Albani et al., *Plant Molec. Biol.* 16: 501 (1991), Twell et al., *Genes & Development* 5: 496 (1991), and Albani et al., *The Plant Journal* 2: 331 (1992). According to the scheme of Mascarenhas, *Ann. Rev. Plant Physiol. Plant Mol. Biol.* 41: 317 (1990), genes expressed during microsporogenesis can be characterized as "early" or "late" genes. Transcripts from early genes are first detectable soon after meiosis and are reduced or undetectable in mature pollen. In contrast, the expression of late genes begins around the time of microspore mitosis and continues as the pollen matures. In addition, it is possible that particular genes expressed during microsporogenesis cannot be classified as either early genes or late genes.

Under Mascarenhas's classification scheme, the Bnm1 gene described herein is an early gene. Therefore, the regulatory element of the Bnm1 gene is functionally distinct from the regulatory elements of late genes such as the maize Zm13 gene (Guerrero et al., supra), the tobacco NTP303 gene (Weterings et al., *Plant Mol. Biol.* 18: 1101 (1992)), the tomato LAT51 gene (McCormick, *Trends Genet.* 7: 298 (1991)), the petunia chalcone flavanone isomerase gene (chiA $P_{A2}$ promoter; van Tunen et al., *The Plant Cell* 2: 393 (1990)), and the *Brassica campestris* Bcp1 gene (Theerakulpisut et al., *The Plant Cell* 3: 1073 (1991)).

Functional differences also can be found within the group of early genes by comparing patterns of mRNA synthesis. For example, the LAT52 gene is expressed in endosperm, LAT59 is expressed in endosperm and roots, while LAT56 is expressed in roots. Twell et al., *Mol. Gen. Genet.* 217: 240 (1989); Wing et al., supra; McCormick, *The Plant Cell* 5: 1265 (1993). In contrast, the Bnm1 gene is not expressed either in roots or in developing seeds. See Example 2. In addition, northern analyses indicate that the level of Bnm1 gene expression is greater than the level of expression of *Brassica napus* genes Bp4, Bp19 and Bp10. Albani et al. (1990, 1991, 1992), supra. See Example 2. This observation suggests that the Bnm1 promoter is stronger than the promoters of the Bp4, Bp19 and Bp10 genes.

In addition, variations in the function of early gene regulatory elements may be revealed by transformation studies. For example, the pollen-specific regulatory element of the Brassica oleracea $SLG_{13}$ gene induces gene expression in the pollen of transgenic plants primarily at the binucleate stage of development. Thorsness et al., *Develop. Biol.* 143: 173 (1991); Dzelzkalns et al., *The Plant Cell* 5: 855 (1993). Moreover, the $SLG_{13}$ regulatory element does not induce gene expression in the tapetum of transgenic plants. Thorsness et al., supra. In contrast, the Bnm1 regulatory element induces gene expression in the microspores of transgenic plants beginning at the uninucleate stage of development, as well as in tapetal cells. See Example 5.

Thus, Bnm1 can be distinguished on a functional basis from other known early genes.

In addition to this functional distinction, a comparison of nucleotide sequences in several databases failed to reveal a nucleotide sequence that was equivalent or similar to the nucleotide sequence of the Bnm1 microspore-specific regulatory element shown in FIG. 3 [SEQ ID NO: 8]. The absence of a match is consistent with the fact that it has not been possible to develop generally accepted principles or structural criteria for recognizing DNA sequences that confer microspore specificity. This is particularly true for regulatory elements of Brassica microspore-specific genes. Consequently, a Brassica microspore-specific regulatory element cannot be isolated from a genomic library by screening for a consensus sequence that confers microspore-specific gene expression.

Hence, the novel microspore-specific regulatory element of the present invention was obtained by isolating cDNA molecules that encode microspore-specific genes and then, using the cDNAs as probes to identify corresponding genes in a suitable genomic library.

3. Isolation of a Regulatory Element from a Microspore-specific Gene

A. Isolation of cDNA Molecules Encoding Microspore-Specific Genes

The first step in the construction of a cDNA library containing microspore-specific genes is to isolate total RNA from microspores. Preferably, RNA is isolated from late uninucleate/early binucleate microspores which have been cultured for four days to induce embryogenesis. Most preferably, such microspores are obtained from *Brassica napus*.

Total RNA can be prepared from microspores using techniques well-known to those in the art. In general, RNA isolation techniques must provide a method for breaking plant cells, a means of inhibiting RNase-directed degradation of RNA, and a method of separating RNA from DNA, protein, and polysaccharide contaminants. For example, total RNA can be isolated from microspores by freezing the tissue in liquid nitrogen, grinding the frozen tissue with a mortar and pestle to lyse the microspores, extracting the ground tissue with a solution of phenol/chloroform to remove proteins, and separating RNA from the remaining impurities by selective precipitation with lithium chloride. See, for example, Ausubel et al. (eds.), CURRENT PROTOCOLS IN MOLECULAR BIOLOGY, pages 4.3.1–4.3.4 (Wiley Interscience 1990) ["Ausubel"]. Also, see Sharrock et al., *Genes and Development* 3: 1745 (1989).

Alternatively, total RNA can be isolated from microspores by extracting ground tissue with guanidinium isothiocyanate, extracting with organic solvents, and separating RNA from contaminants using differential centrifugation. See, for example, Strommer et al., "Isolation and characterization of Plant mRNA," in METHODS IN PLANT MOLECULAR BIOLOGY AND BIOTECHNOLOGY, Glick et al. (eds.), pages 49–65 (CRC Press 1993).

In order to construct a cDNA library, poly(A)$^+$ RNA must be isolated from a total RNA preparation. Poly(A)$^+$ RNA can be isolated from total RNA by using the standard technique of oligo(dT)-cellulose chromatography. See, for example, Strommer et al., supra.

Double-stranded cDNA molecules are synthesized from poly(A)+ RNA using techniques well-known to those in the art. See, for example, Ausubel at pages 5.5.2–5.6.8. Moreover, commercially available kits can be used to synthesize double-stranded cDNA molecules. For example, such kits are available from GIBCO/BRL (Gaithersburg, Md.), Clontech Laboratories, Inc. (Palo Alto, Calif.), Promega Corporation (Madison, Wis.) and Stratagene® Cloning Systems (La Jolla, Calif.).

Various cloning vectors are appropriate for the construction of a microspore cDNA library. For example, a cDNA library can be prepared in a vector derived from bacteriophage, such as a λgt10 vector. Huynh et al., "Constructing and Screening cDNA Libraries in λgt10 and λgt11, " in *DNA Cloning: A Practical Approach*, Vol. I, Glover (ed.), pages 49–78 (IRL Press, 1985).

Alternatively, double-stranded cDNA molecules can be inserted into a plasmid vector, such as a pBluescript® vector (Stratagene® Cloning Systems; La Jolla, Calif.), a LambdaGEM®-4 (Promega Corp.) or other commercially available vectors. Suitable cloning vectors also can be obtained from the American Type Culture Collection (Rockville, Md.).

In order to amplify the cloned cDNA molecules, the cDNA library is inserted into a procaryotic host, using standard techniques. For example, the microspore cDNA library can be introduced into competent *E. coli* DH5 cells, which can be obtained from GIBCO/BRL (Gaithersburg, Md.).

Differential screening can be used to isolate cDNA clones encoding microspore-specific genes from the cDNA library. For example, single-stranded cDNA probes can be synthesized in the presence of radioactive nucleotides using poly (A)+ RNA isolated from microspores which have been treated to induce embryogenesis ("Mi-RNA") or from microspores which have been treated to eliminate the embryogenic response ("Mx-RNA"). cDNA clones that hybridize with cDNA probes synthesized from Mi-RNA, but not with Mx-cDNA probes, are isolated for further analysis. The technique of differential screening is well-known to those in the art. See, for example, Sargent, "Isolation of Differentially Expressed Genes," in GUIDE TO MOLECULAR CLONING TECHNIQUES, Berger et al. (eds.), pages 423–432 (Academic Press, 1987); Tedder et al., *Proc. Natl. Acad. Sci. USA* 85: 208 (1988). Example 1 illustrates the use of this technique.

The basic approach for obtaining microspore-specific cDNA clones can be modified by constructing a subtracted cDNA library which is enriched in microspore-specific cDNA clones. Hedrick et. al., *Nature* 308: 149 (1984). For example, double-stranded cDNA with EcoRI ends can be prepared from Mi-RNA and mixed with a 50-fold excess of small, blunt-ended cDNA fragments prepared from Mx-RNA. The mixture of cDNAs is heated to melt double-stranded cDNA, single-stranded cDNAs are allowed to hybridize, and double-stranded cDNA molecules are inserted into the EcoRI site of a cloning vector. Under these conditions, the only Mi-cDNA molecules that are likely to regenerate double-stranded fragments with an EcoRI site at each end are those cDNAs that lack complementary fragments in the Mx-cDNA. Ausubel at pages 5.8.9.–5.8.15.

cDNA clones can be analyzed using a variety of techniques such as Northern analysis, Southern analysis, restriction mapping and sequence analysis, as illustrated in Examples 1–3.

B. Isolation of Microspore-Specific Genes from a Genomic Library

The methodology, described above, can be used to isolate cDNA clones encoding proteins that are expressed in microspore tissue. A microspore-specific cDNA clone, such as the Bnm1 cDNA clone, may be used to disrupt microspore function in antisense constructs, following the general approaches described below. In addition, such cDNA clones can be used as probes to isolate the corresponding genes from a genomic library.

A plant genomic DNA library can be prepared by means well-known in the art. See, for example, Slightom et al. "Construction of λ Clone Banks," in METHODS IN PLANT MOLECULAR BIOLOGY AND BIOTECHNOLOGY, Glick et al. (eds.), pages 121–146 (CRC Press, 1993). A preferred source of plant genomic DNA is *Brassica napus* DNA. Genomic DNA can be isolated from *Brassica napus* tissue, for example, by lysing plant tissue with the detergent Sarkosyl, digesting the lysate with proteinase K, clearing insoluble debris from the lysate by centrifugation, precipitating nucleic acid from the lysate using isopropanol, and purifying resuspended DNA on a cesium chloride density gradient. Ausubel at pages 2.3.1–2.3.3.

DNA fragments that are suitable for the production of a genomic library can be obtained by the random shearing of genomic DNA or by the partial digestion of genomic DNA with restriction endonucleases. See, for example, Ausubel at pages 5.3.2–5.4.4, and Slightom et al., supra.

Genomic DNA fragments can be inserted into a vector, such as a bacteriophage or cosmid vector, in accordance with conventional techniques, such as the use of restriction enzyme digestion to provide appropriate termini, the use of alkaline phosphatase treatment to avoid undesirable joining of DNA molecules, and ligation with appropriate ligases. Techniques for such manipulation are disclosed by Slightom et al., supra, and are well-known in the art. Also see Ausubel at pages 3.0.5–3.17.5.

Alternatively, a plant genomic library can be obtained from a commercial source such as Clontech Laboratories, Inc. (Palo Alto, Calif.) or Stratagene® Cloning Systems (La Jolla, Calif.).

A library containing genomic clones is screened with one or more microspore-specific cDNA clones using standard techniques. See, for example, Ausubel at pages 6.0.3–6.6.1; Slightom et al., supra; Raleigh et al., *Genetics* 122: 279 (1989). Example 4 presents the method that was used to screen a *Brassica napus* genomic library.

C. Identification of a Microspore-Specific Regulatory Element

Genomic clones can be analyzed using a variety of techniques such as restriction analysis, Southern analysis, primer extension analysis, and DNA sequence analysis. Primer extension analysis or S1 nuclease protection analysis, for example, can be used to localize the putative start site of transcription of the cloned gene. Ausubel at pages 4.8.1–4.8.5; Walmsley et al., "Quantitative and Qualitative Analysis of Exogenous Gene Expression by the S1 Nuclease Protection Assay," in METHODS IN MOLECULAR BIOLOGY, VOL. 7: GENE TRANSFER AND EXPRESSION PROTOCOLS, Murray (ed.), pages 271–281 (Humana Press Inc. 1991). Example 4 illustrates the use of Southern analysis, restriction mapping and sequence analysis to characterize the Bnm1 gene.

Structural analysis per se cannot lead to the identification of a microspore-specific regulatory element associated with the cloned Bnm1 gene because a model for *Brassica napus* microspore-specific regulatory sequences has not been developed. Thus, the regulatory element must be identified using functional analysis.

The general approach of such functional analysis involves subcloning fragments of the genomic clone into an expression vector which contains a reporter gene, introducing the expression vector into various plant tissues, and assaying the tissue to detect the transient expression of the reporter gene. The presence of a microspore-specific regulatory element in the genomic subclone is verified by the observation of reporter gene expression in microspore tissue, and the absence of reporter gene expression in non-microspore tissue, such as pistil or sepal tissues.

Methods for generating fragments of a genomic clone are well-known. Preferably, enzymatic digestion is used to form nested deletions of genomic DNA fragments. See, for example, Ausubel at pages 7.2.1–7.2.20; An et al., "Techniques for Isolating and Characterizing Transcription Promoters, Enhancers, and Terminators," in METHODS IN PLANT MOLECULAR BIOLOGY AND BIOTECHNOLOGY, Glick et al. (eds.), pages 155–166 (CRC Press 1993).

As an example, the possibility that the regulatory element resides "upstream," or 5'-ward, of the transcriptional start site can be tested by subcloning a DNA fragment that contains the upstream region, digesting the DNA fragment in either the 5' to 3' direction or in the 3' to 5' direction to produce nested deletions, and subcloning the small fragments into expression vectors for transient expression.

The selection of an appropriate expression vector will depend upon the method of introducing the expression vector into host cells. Typically, an expression vector contains: (1) prokaryotic DNA elements coding for a bacterial replication origin and an antibiotic resistance marker to provide for the growth and selection of the expression vector in the bacterial host; (2) eukaryotic DNA elements that control initiation of transcription, such as a promoter; (3) DNA elements that control the processing of transcripts, such as a transcription termination/polyadenylation sequence; and (4) a reporter gene that is operably linked to the DNA elements that control transcription initiation. Useful reporter genes include β-glucuronidase, β-galactosidase, chloramphenicol acetyl transferase, luciferase, and the like. Preferably, the reporter gene is either the β-glucuronidase (GUS) gene or the luciferase gene. General descriptions of plant expression vectors and reporter genes can be found in Gruber et al., "Vectors for Plant Transformation," in METHODS IN PLANT MOLECULAR BIOLOGY AND BIOTECHNOLOGY, Glick et al. (eds.), pages 89–119 (CRC Press 1993). Moreover, GUS expression vectors and GUS gene cassettes are available from Clontech Laboratories, Inc. (Palo Alto, Calif.), while luciferase expression vectors and luciferase gene cassettes are available from Promega Corporation (Madison, Wis.).

Expression vectors containing test genomic fragments can be introduced into protoplasts, or into intact tissues or isolated cells. Preferably, expression vectors are introduced into intact tissues. General methods of culturing plant tissues are provided, for example, by Miki et al., "Procedures for Introducing Foreign DNA into Plants," in METHODS IN PLANT MOLECULAR BIOLOGY AND BIOTECHNOLOGY, Glick et al. (eds.), pages 67–88 (CRC Press, 1993).

Methods of introducing expression vectors into plant tissue include the direct infection or co-cultivation of plant tissue with *Agrobacterium tumefaciens*. Horsch et al., *Science* 227: 1229 (1985). Descriptions of Agrobacterium vector systems and methods for Agrobacterium-mediated gene transfer are provided by Gruber et al., supra, Miki et al., supra, and Moloney et al., *Plant Cell Reports* 8: 238 (1989).

Alternatively, expression vectors are introduced into plant tissues using a direct gene transfer method such as microprojectile-mediated delivery, DNA injection, electroporation, and the like. See, for example, Gruber et al., supra; Miki et al., supra; Klein et al., *Biotechnology* 10: 268 (1992). For example, expression vectors can be introduced into plant tissues using microprojectile-mediated delivery with a biolistic device.

Transformation studies have been used to identify DNA sequences that regulate gene expression in a microspore-specific manner. In particular, a microspore-specific regulatory element was found to reside within an 820 base pair DNA fragment which is located immediately upstream of the Bnm1 start site of translation. The nucleotide sequence of a microspore-specific regulatory element is provided in FIG. 3 [SEQ ID NO: 8]. Thus, the present invention encompasses a DNA molecule having a nucleotide sequence of SEQ ID NO: 8 and having the function of a microspore-specific regulatory element.

Variants of the microspore-specific regulatory element can be produced by deleting, adding and/or substituting nucleotides for the nucleotides recited in SEQ ID NO: 8. Such variants can be obtained, for example, by oligonucleotide-directed mutagenesis, linker-scanning mutagenesis, mutagenesis using the polymerase chain reaction, and the like. Ausubel at pages 8.0.3–8.5.9. Also see generally, McPherson (ed.), DIRECTED MUTAGENESIS: A PRACTICAL APPROACH, IRL Press (1991). Thus, the present invention also encompasses DNA molecules comprising nucleotide sequences that have substantial sequence similarity with SEQ ID NO: 8 and function as a microspore-specific promoter.

Moreover, deletion analyses can be performed to further localize one or more microspore-specific regulatory elements within the 820 base pair microspore-specific regulatory element. Thus, the present invention also encompasses "functional fragments" of SEQ ID NO: 8 which can be used as microspore-specific regulatory elements.

4. Use of a Microspore-Specific Regulatory Element to Control Pollen Production

A. Production of Male-Sterile Plants

One object of the present invention is to provide a means to control pollen production using a microspore-specific regulatory element. In particular, the present invention encompasses the production of male-sterile plants using Bnm1 regulatory sequences to stimulate the expression of a foreign gene in microspores. The Bnm1 microspore-specific regulatory element induces gene expression from immediately prior to the binucleate stage through the trinucleate stage of microspore development. Since expression is confined to a limited tissue and stage, the use of the Bnm1 regulatory element to induce male sterility obviates regulatory concerns about accumulation of a foreign gene product in various other tissues, including the edible portions of plants.

One general approach to induce male sterility is to construct an expression vector in which the microspore-specific regulatory element is operably linked to a nucleotide sequence that encodes a protein capable of disrupting microspore function. Proteins capable of disrupting microspore function include proteins that inhibit the synthesis of macromolecules that are essential for cellular function, enzymes that degrade macromolecules that are essential for cellular function, proteins that alter the biosynthesis or metabolism of plant hormones, and proteins that inhibit a specific function of microspores.

For example, an expression vector can be constructed in which the microspore-specific regulatory element is operably linked to a nucleotide sequence that encodes an inhibitor of protein synthesis. Diphtheria toxin, for example, is a well-known inhibitor of protein synthesis in eukaryotes. DNA molecules encoding the diphtheria toxin gene can be obtained from the American Type Culture Collection (Rockville, Md.), ATCC No. 39359 or ATCC No. 67011. As discussed below, pokeweed antiviral protein is another suitable inhibitor of protein synthesis.

Alternatively, the disruption of microspore function can be achieved using DNA sequences that encode enzymes capable of degrading a biologically important macromolecule. For example, Mariani et al., *Nature* 347: 737 (1990), have shown that expression in the tapetum of either *Aspergillus oryzae* RNase-T1 or an RNase of *Bacillus amyloliquefaciens*, designated "barnase," induced destruction of the tapetal cells, resulting in male infertility. Thus, microspore function can be disrupted using an expression vector containing a microspore-specific regulatory element which is operably linked to a barnase gene. Other suitable enzymes include DNases, proteases and lipases.

Genes encoding such microspore-disrupting enzymes can be obtained by chemical synthesis using published nucleotide sequences. RNase-T1 and barnase genes may be obtained, for example, by synthesizing the genes with mutually priming long oligonucleotides. See, for example, Ausubel at pages 8.2.8 to 8.2.13. Also, see Wosnick et al., *Gene* 60: 115 (1987). Moreover, current techniques using the polymerase chain reaction provide the ability to synthesize genes as large as 1.8 kilobases in length. Adang et al., *Plant Molec. Biol.* 21: 1131 (1993); Bambot et al., *PCR Methods and Applications* 2: 266 (1993). Quaas et al., *Eur. J. Biochem.* 173: 617 (1988), describe the chemical synthesis of the RNase-T1, while the nucleotide sequence of the barnase gene is disclosed in Hartley, *J. Molec. Biol.* 202: 913 (1988).

In an alternative approach, pollen function is disrupted by altering the metabolism of plant hormones, such as auxins and gibberellins. For example, the rolB gene of *Agrobacterium rhizogenes* codes for an enzyme that interferes with auxin metabolism by catalyzing the release of free indoles from indoxyl-β-glucosides. Estruch et al., *EMBO J.* 11: 3125 (1991). Spena et al., *Theor. Appl. Genet.* 84: 520 (1992), have shown that the anther-specific expression of the rolB gene in tobacco resulted in plants having increased levels of indole-3-acetic acid, decreased gibberellin activity, and shrivelled anthers in which pollen production was severely decreased. Since expression of the rolB gene in microspores is expected to increase levels of indole-3-acetic acid in anther tissue, the rolB gene is another example of a gene that is useful for the control of pollen production. Slightom et al., *J. Biol. Chem.* 261: 108 (1985), disclose the nucleotide sequence of the rolB gene.

In order to express a protein that disrupts microspore function, an expression vector is constructed in which a DNA sequence encoding the protein is operably linked to DNA sequences that regulate gene transcription in a microspore-specific manner. The general requirements of an expression vector are described above in the context of a transient expression system. Here, however, the objective is to introduce the expression vector into plant embryonic tissue in such a manner that a foreign protein will be expressed at a later stage of development in microspores of the adult plant. Mitotic stability can be achieved using plant viral vectors that provide epichromosomal replication.

An alternative and preferred method of obtaining mitotic stability is provided by the integration of expression vector sequences into the host chromosome. Such mitotic stability can be provided by the Agrobacterium-mediated transformation technique illustrated in Example 5, below.

Transcription of the foreign gene may be controlled by a promoter of a microspore-specific gene or by a viral promoter, such as a Cauliflower Mosaic Virus (CaMV) promoter, a Figwort Mosaic Virus promoter, and the like. Gruber et al., supra. Preferably, the promoter is a promoter of a microspore-specific gene or the CaMV 35S core promoter. More preferably, the promoter is a promoter of a microspore-specific gene and in particular, the Bnm1 promoter.

Alternatively, transcription of the foreign gene may be controlled by a promoter of an anther-specific gene. In this way, foreign genes capable of disrupting cellular function can be expressed in microspores and anther cells. Anther-specific promoters and genes are known in the art. See, for example, McCormick et al., "Anther-Specific Genes: Molecular Characterization and Promoter Analysis in Transgenic Plants," in PLANT REPRODUCTION: FROM FLORAL INDUCTION TO POLLINATION, Lord et al. (eds.), pages 128–135 (1989); Scott et al., International Application Publication No. WO 92/11379 (1992); van der Meer et al., *The Plant Cell* 4: 253 (1992). The above-described methods can be used to chemically synthesize an anther-specific promoter having a published nucleotide sequence.

In order to select transformed cells, the expression vector contains a selectable marker gene, such as a herbicide resistance gene or an antibiotic resistance gene. For example, such genes may confer resistance to phosphinothricine, glyphosate, sulfonylureas, atrazine, imidazolinone or aminoglycoside antibiotics such as neomycin, kanamycin and G418 (genticin). Preferably, the selectable marker gene is the neomycin phosphotransferase gene (nptII gene).

The expression vector can contain cDNA sequences encoding a foreign protein under the control of a microspore-specific regulatory element, as well as the selectable marker gene under control of a constitutive promoter. Alternatively, the selectable marker gene can be delivered to host cells in a separate selection expression vector by co-transformation with both vectors.

In an alternative approach, male sterility can be induced by the use of an expression vector in which the microspore-specific regulatory element is operably linked to a nucleotide sequence that encodes an antisense RNA. The binding of antisense RNA molecules to target mRNA molecules results in hybridization arrest of translation. Paterson, et al., *Proc. Natl. Acad. Sci. USA*, 74: 4370 (1987). Thus, a suitable antisense RNA molecule would have a sequence that is complementary to that of a mRNA species encoding a protein that is necessary for cellular function.

For example, antisense RNA molecules can be used to inhibit the translation of mRNAs encoding actin, tubulin, ubiquitin, ubiquitin conjugating enzyme, ubiquitin carrier protein or elongation factors. DNA molecules encoding such genes can be isolated using standard techniques. For example, plant actin genes are described by Shah et al., *Proc. Nat'l Acad. Sci. USA* 79: 1022 (1982) and by Baird et al., *EMBO J.* 6: 3223 (1987). Plant tubulin genes are described by Raha et al., *Plant Mol. Biol.* 9: 565 (1987), Ludwig et al., *Proc. Nat'l Acad. Sci. USA* 84: 5833 (1987), and Yamada et al., *Plant Physiol.* 103: 1467 (1993). Plant ubiquitin genes have been isolated by Gausing et al., *Eur. J. Biochem.* 158: 57 (1986), and by Xia et al., *Plant Physiol.* 104: 805 (1994). Pramanik et al., *Plant Physiol.* 102: 1049 (1993), report the cloning of alfalfa ubiquitin carrier protein, while Picton et al., *Plant Physiol.* 103: 1471 (1993), isolated a tomato ubiquitin conjugating enzyme. The cloning of a barley elongation factor gene has been described by Sutton et al., *Plant Physiol.* 104: 807 (1994). Moreover, DNA molecules encoding useful genes can be synthesized using published nucleotide sequences, as discussed above.

In addition, antisense RNA molecules can be directed to mRNAs that encode proteins essential for pollen development. For example, chalcone synthase (CHS) catalyzes the initial step in the biosynthesis of flavonoids, and a lack of CHS activity has been correlated with abnormal pollen function and/or development. Coe et al., *J. Hered.* 72: 318 (1981); Taylor et al., *J. Hered.* 83: 11 (1992); van der Meer et al., *The Plant Cell* 4: 253 (1992). Significantly, flavonoid-deficient pollen do not function in self-crosses. Taylor et al., supra. Therefore, male sterility can be induced by the inhibition of flavonoid biosynthesis using an expression vector that produces antisense RNA for the 3' untranslated region of chalcone synthase A gene. van der Meer et al., supra. The cloning and characterization of the chalcone synthase A gene is disclosed by Koes et al., *Gene* 81: 245 (1989), and by Koes et al., *Plant Molec. Biol.* 12: 213 (1989).

Alternatively, an expression vector can be constructed in which the microspore-specific regulatory element is operably linked to a nucleotide sequence that encodes a ribozyme. Ribozymes can be designed to express endonuclease activity that is directed to a certain target sequence in a mRNA molecule. For example, Steinecke et al., *EMBO J.* 11: 1525 (1992), achieved up to 100% inhibition of neomycin phosphotransferase gene expression by ribozymes in tobacco protoplasts. More recently, Perriman et al., *Antisense Research and Development* 3: 253 (1993), inhibited chloramphenicol acetyl transferase activity in tobacco protoplasts using a vector that expressed a modified hammerhead ribozyme. In the context of the present invention, appropriate target RNA molecules for ribozymes include mRNA species that encode proteins essential for microspore function, as described above.

In a further alternative approach, expression vectors can be constructed in which a microspore-specific regulatory element directs the production of RNA transcripts capable of promoting RNase P-mediated cleavage of target mRNA molecules. According to this approach, an external guide sequence can be constructed for directing the endogenous ribozyme, RNase P, to a particular species of intracellular mRNA, which is subsequently cleaved by the cellular ribozyme. Altman et al., U.S. Pat. No. 5,168,053. Yuan et al., *Science* 263: 1269 (1994). Preferably, the external guide sequence comprises a ten to fifteen nucleotide sequence complementary to an mRNA species that encodes a protein essential for microspore function, and a 3'-NCCA nucleotide sequence, wherein N is preferably a purine. Id. The external guide sequence transcripts bind to the targeted mRNA species by the formation of base pairs between the mRNA and the complementary external guide sequences, thus promoting cleavage of mRNA by RNase P at the nucleotide located at the 5'-side of the base-paired region. Id.

Alternatively, antisense genes, ribozyme genes and external guide sequence genes can be regulated by a combination of a microspore-specific regulatory element and a promoter of an anther-specific gene.

All microspores of the transgenic plant may not express the foreign gene that disrupts cellular function. However, Example 5 presents evidence that the Bnm1 microspore-specific regulatory element also induces the expression of a foreign gene in tapetal cells, which are essential for microspore development. Thus, Bnm1 regulatory sequences are particularly suitable for ensuring complete male sterility.

Nevertheless, additional mechanisms can be devised to disrupt the function of microspores that do not express the foreign gene. For example, the foreign gene can encode a protein that stimulates the production of a diffusible molecule capable of disrupting the function of viable microspores. An increase in indole-3-acetic acid levels by rolB gene expression or the production of diphtheria toxin would accomplish this objective. Moreover, the Bnm1 microspore-specific regulatory element can be operably linked to DNA sequences encoding other functionally stable macromolecules that can degrade microspores, pollen, or structural components thereof (e.g., cell walls). In this way, the macromolecules produced in one microspore are introduced into the surrounding locule following microspore degradation, and act on other microspores or pollen.

This approach is particularly attractive in the case of heterozygotes in which only 50% of the developing pollen grains express the disruptive gene. Again, the function of microspores or pollen grains that do not contain the foreign gene would be disrupted by the action of macromolecules released from microspores or pollen grains that express the foreign gene. Since the Bnm1 regulatory element stimulates gene expression in a tissue-dependent manner, the remaining tissues of the sterile plant can develop normally.

Finally, an expression vector can be constructed in which the expression of the foreign gene is controlled by a Bnm1 regulatory element and an anther-specific promoter, as discussed above.

B. Restoration of Male Fertility in the F1 Hybrid

The above-described methods can be used to produce transgenic male-sterile plants for the production of F1 hybrids in large-scale directed crosses between inbred lines. If all male gamete cells of the transgenic male-sterile plants do not contain the foreign gene that disrupts microspore function, then a proportion of F1 hybrids will have a male-fertile phenotype. On the other hand, F1 hybrids will have a male-sterile phenotype if the foreign gene is present in all male gamete cells of the transgenic male-sterile plants because sterility induced by the foreign gene would be dominant. Moreover, F1 hybrids will have a male-sterile phenotype if expression of the foreign gene results in the disruption of neighboring cells. Thus, it is desirable to use a male fertility restoration system to provide for the production of male-fertile F1 hybrids. Such a fertility restoration system has particular value when the harvested product is seed.

One approach to male fertility restoration would be to cross transgenic male-sterile plants with transgenic male-fertile plants which contain a fertility restoration gene under the control of a microspore-specific regulatory element. For example, the fertility restoration gene can encode a protein specifically targeted to the product of the cellular disrupter gene. As an illustration, Mariani et al., *Nature* 357: 384 (1992), crossed male-fertile plants that expressed a barnase inhibitor in anther cells, designated "barstar," with male-sterile plants that expressed barnase in anther cells. Hartley, *J. Mol. Biol.* 202: 913 (1988), discloses the nucleotide sequence of barstar.

Alternatively, the fertility restoration gene can be used to produce RNA molecules that are targeted to mRNAs encoding the cellular disrupter protein. For example, male fertility restoration can be achieved by expressing diphtheria toxin ribozymes or antisense RNA in male-fertile plants to neutralize the effects of diphtheria toxin in male-sterile plants. Thus, male fertility can be restored in the F1 hybrids by producing a male-fertile transgenic plant that synthesizes a particular species of RNA molecule or polypeptide to counteract the effects of the particular foreign gene expressed in the male-sterile transgenic plants.

In an alternative approach, male fertility can be restored by application of a chemical compound. As discussed above, male sterility can be induced by blocking the expression of chalcone synthase to inhibit flavonoid biosynthesis. The application of flavonol aglycones can be used to complement the biochemical defect and restore pollen function. Mo et al., *Proc. Nat'l Acad. Sci. USA* 89: 1713 (1992); Vogt et al., *The Plant Cell* 6: 11 (1994). Preferred flavonol aglycones, such as kaempferol, have an unsaturated bond between the carbons at positions two and three in the C ring of the flavonoid skeleton, as well as an unsubstituted hydroxyl group in position three of ring C. Vogt et al., supra.

5. Use of a Microspore-Specific Regulatory Element to Inhibit Plant Disease

Another object of the present invention is to provide a means to control disease caused by pests. In particular, the present invention encompasses the production of transgenic plants comprising expression vectors in which Bnm1 regulatory sequences stimulate the expression of macromolecules useful for defense against viruses and insects.

Approximately 20% of plant viruses are transmitted from generation to generation in the seed. Matthews, PLANT VIROLOGY, 3rd Edition, (Academic Press, Inc. 1991); Mink, *Ann. Rev. Phytopathol.* 31: 375 (1993). Seed transmission is achieved either by direct invasion of the embryo or by an indirect invasion of the embryo via infected gametes. According to Mink, supra, there are at least nine viruses that appear to spread plant-to-plant through pollen, and at least four viroids that are transmitted through pollen to seed and female plants. Thus, the Bnm1 microspore-specific regulatory element can be used to inhibit the transmission of these viruses and viroids.

In one approach for providing protection against viral infections, a Bnm1 regulatory element is used to stimulate the expression of a viral coat protein. The accumulation of viral coat proteins in transformed plant cells provides resistance to viral infection and/or disease development by the virus from which the coat protein gene was derived, as well as by related viruses. See Beachy et al., *Ann. Rev. Phytopathol.* 28: 451 (1990); Beachy, "Virus Resistance Through Expression of Coat Protein Genes," in BIOTECHNOLOGY IN PLANT DISEASE CONTROL, 3rd Edition, Chet (Ed.), pages 89–104 (Wiley-Liss, Inc. 1993). For example, coat protein-mediated resistance has been conferred upon transformed plants against alfalfa mosaic virus, cucumber mosaic virus, tobacco streak virus, potato virus X, potato virus Y, tobacco etch virus, tobacco rattle virus, and tobacco mosaic virus. Id.

Alternatively, protection against viral disease can be achieved using a vector comprising mammalian 2'–5' oligoadenylate synthetase operably linked to a microspore-specific regulatory element. Truve et al., *Bio/Technology* 11: 1048 (1993), disclose the cloning and nucleotide sequence of a rat cDNA encoding 2'–5' oligoadenylate synthetase, a component of the mammalian interferon-induced antivirus response. Truve et al., also disclose that transgenic plants expressing 2'–5' oligoadenylate synthetase are protected against viral infection under field conditions.

In a third approach to providing protection against viral infection, a microspore-specific regulatory element of the present invention is used to direct the expression of viral genome antisense RNA. For example, antisense RNA can be used to confer resistance to cucumber mosaic virus, as disclosed by Rezaian et al., *Plant Molec. Biol.* 11: 463 (1988). Alternatively, antisense RNA can be used to confer resistance against tomato golden mosaic virus, as disclosed by Day et al., *Proc. Nat'l. Acad. Sci.* 88: 6721 (1991).

In a fourth approach to providing protection against viral infection, a microspore-specific regulatory element is used to direct the expression of pokeweed antiviral protein (PAP), a ribosome-inhibiting protein found in the cell walls of *Phytolacca americana*. Lodge et al., *Proc. Nat'l Acad. Sci USA* 90: 7089 (1993), show that PAP-expressing transgenic plants are resistant to a broad spectrum of plant viruses. Lodge et al. also disclose a method for isolating PAP cDNA.

The present invention also contemplates the use of a Bnm1 regulatory element to provide protection against insect pests, such as thrips, the pollen-feeding arthropods of the order Thysanoptera. According to this approach, a Bnm1 regulatory element is used to stimulate the expression of insecticidal toxin genes. For example, the gram-positive bacterium *Bacillus thuringiensis* produces polypeptides that are toxic to a variety of insect pests, but have no activity against vertebrates and beneficial insects. Thompson, "Biological Control of Plant Pests and Pathogens: Alternative Approaches," in BIOTECHNOLOGY IN PLANT DISEASE CONTROL, Chet (ed.), pages 275–290 (Wiley-Liss, Inc. 1993). Suitable *Bacillus thuringiensis* toxins include cryIA δ-endotoxins which are highly toxic to lepidopteran insects and cryIIIA δ-endotoxins which are highly toxic to coleopteran insects.

Geiser et al., *Gene* 48: 109 (1986), disclose the cloning and nucleotide sequence of a cryIA(b) δ-endotoxin gene. The transformation of plants with vectors comprising a cryIA(b) δ-endotoxin gene has been described by Williams et al., *Bio/Technology* 10: 540 (1992), Koziel et al., *Bio/Technology* 11: 194 (1993), and Fujimoto et al., *Bio/Technology* 11: 1151 (1993). Lereclus et al., *Bio/Technology* 10: 418 (1992), disclose the construction of a plasmid comprising structural genes encoding for cryIIIA and cryIAc. In addition, Adang et al., *Plant Molec. Biol.* 21: 1131 (1993), disclose the nucleotide sequence of a synthetic cryIIIA gene which was designed for optimal expression in plant cells. Moreover, DNA molecules encoding δ-endotoxin genes can be purchased from American Type Culture Collection (Rockville, Md.), under ATCC accession Nos. 40098, 67136, 31995 and 31998.

As an illustration, the European corn borer, *Ostrinia nubilalis*, is a major pest of maize in North America and Europe. After hatching, most second brood neonate corn borer larvae feed on pollen accumulated at the leaf axils and on sheath and collar tissues. Once the larvae begin feeding inside the collar, they are protected from the effects of chemical pesticides. Koziel et al., supra, showed that transgenic maize plants expressing the cryIA(b) gene were resistant to repeated heavy infestations of the corn borer.

The following list provides other insecticidal toxins which are suitable for microspore-specific expression.

(1) A vitamin-binding protein such as avidin. See U.S. patent application Ser. No. 07/911,864, now abandoned, which teaches the use of avidin and avidin homologues as larvicides against insect pests.

(2) An enzyme inhibitor, for example, a protease inhibitor or an amylase inhibitor. See, for example, Abe et al., *J. Biol. Chem.* 262: 16793 (1987) (nucleotide sequence of rice cysteine proteinase inhibitor), Huub et al., *Plant Molec. Biol.* 21: 985 (1993) (nucleotide sequence of cDNA encoding tobacco proteinase inhibitor I), and Sumitani et al., *Biosci. Biotech. Biochem.* 57: 1243 (1993) (nucleotide sequence of *Streptomyces nitrosporeus* α-amylase inhibitor).

(3) An insect-specific hormone or pheromone such as an ecdysteroid and juvenile hormone, a variant thereof, a mimetic based thereon, or an antagonist or agonist thereof. See, for example, the disclosure by Hammock et al., *Nature* 344: 458 (1990), of *baculovirus* expression of cloned juvenile hormone esterase, an inactivator of juvenile hormone.

(4) An insect-specific peptide or neuropeptide which, upon expression, disrupts the physiology of the affected pest. For example, see the disclosures of Regan, *J. Biol. Chem.* 269: 9 (1994) (expression cloning yields DNA coding for insect diuretic hormone receptor), and Pratt et al., *Biochem. Biophys. Res. Comm.* 163: 1243 (1989) (an allostatin is identified in *Diploptera puntata*). See also U.S. Pat. No. 5,266,317 to Tomalski et al., who disclose genes encoding insect-specific, paralytic neurotoxins.

(5) An insect-specific venom produced in nature by a snake, a wasp, etc. For example, see Pang et al., *Gene* 116: 165 (1992), for disclosure of heterologous expression in plants of a gene coding for a scorpion insectotoxic peptide.

(6) An enzyme responsible for an hyperaccumulation of a monterpene, a sesquiterpene, a steroid, hydroxamic acid, a phenylpropanoid derivative or another non-protein molecule with insecticidal activity.

(7) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under accession Nos. 39637 and 67152. See also Kramer et al., *Insect Biochem. Molec. Biol.* 23: 691 (1993), who teach the nucleotide sequence of a cDNA encoding tobacco hookworm chitinase, and Kawalleck et al., *Plant Molec. Biol.* 21: 673 (1993), who provide the nucleotide sequence of the parsley ubi4-2 polyubiquitin gene.

(8) A molecule that stimulates signal transduction. For example, see the disclosure by Botella et al., *Plant Molec. Biol.* 24: 757 (1994), of nucleotide sequences for mung bean calmodulin cDNA clones, and Griess et al., *Plant Physiol.* 104: 1467 (1994), who provide the nucleotide sequence of a maize calmodulin cDNA clone.

(9) An insect-specific antibody or an immunotoxin derived therefrom. Thus, an antibody targeted to a critical metabolic function in the insect gut would inactivate an affected enzyme, killing the insect. Cf. Taylor et al., Abstract #497, SEVENTH INT'L SYMPOSIUM ON MOLECULAR PLANT-MICROBE INTERACTIONS (1994) (enzymatic inactivation in transgenic tobacco via production of single-chain antibody fragments).

The present invention, thus generally described, will be understood more readily by reference to the following examples, which are provided by way of illustration and are not intended to be limiting of the present invention.

EXAMPLE 1

Construction and Screening of a *Brassica napus* Microspore cDNA Library

Late uninucleate/early binucleate *Brassica napus* cv Topas microspores were cultured for four days at 32.5° C. to induce embryogenesis. Poly(A)⁺ RNA was isolated from the microspores using a guanidinium isothiocyanate procedure as described by Ouellet et al., *Plant Journal* 2: 321 (1992). Double stranded cDNA was synthesized from poly(A)⁺ RNA using the Riboclone® cDNA Synthesis System (Promega Corp.; Madison, Wis.) and cloned into the LambdaGEM®-4 cloning vector (Promega Corp.).

The cDNA library was screened differentially for microspore-specific clones by probing duplicate lifts with $^{32}$P-labeled microspore RNA used for library construction (Mi-RNA) or with $^{32}$P-labeled RNA from microspores subjected to 25° C. for 24 hours and then 32° C. for three days to eliminate the embryogenic response (Mx-RNA). Three cDNA clones (Mi-cDNA 3, 4 and 5) that hybridized to Mi-RNA, but not to the Mx-RNA, were purified and further characterized.

A Southern blot of each isolated cDNA clone was hybridized with $^{32}$P-labeled cDNA probes representing the total microspore cDNA library. Napin DNA and lambda vector arms were included on the blot as negative controls. Both Mi-cDNA 3 and Mi-cDNA 4 hybridized with the total cDNA probe and were found to contain inserts of about 800 base pairs. Nucleotide sequence analysis revealed that Mi-cDNA 3 and Mi-cDNA 4 were identical, and probably contained full-length cDNA inserts because both cDNAs terminated at the same nucleotide. The microspore-specific cDNA clone was designated Bnm1. The nucleotide sequence of Bnm1 cDNA [SEQ ID NO: 1] with its corresponding amino sequence [SEQ ID NO: 2] is shown in FIG. 1.

EXAMPLE 2

Northern Analysis with the Bnm1 cDNA Probe

Northern analyses were performed to characterize the expression pattern of the Bnm1 gene. These studies revealed that Bnm 1 cDNA hybridized with RNA from whole buds, flowers and anthers, but did not hybridize with RNA isolated from roots, stems, leaves, pistils and developing seeds. Expression of Bnm1 RNA was very strong in trinucleate and binucleate microspores but essentially absent in uninucleate and tetrad stages of microspore development. Northern analyses results also indicate that Bnm1 RNA is expressed to a greater extent throughout microspore development, as compared with the Brassica microspore-specific clones Bp4, Bp10 and Bp19. Albani et al., *Plant Molecular Biology* 15: 605 (1990); Albani et al., *Plant Molecular Biology* 16: 501 (1991); Albani et al., *The Plant Journal* 2: 331 (1992).

To further characterize the Bnm1 clone, uninucleate microspores were either cultured at 32.50° C. for four days to induce embryogenesis or cultured at 240° C. for four days to allow pollen development. Microspore embryos were isolated at the globular, heart, torpedo and cotyledonary stages of development. Northern analysis of RNA samples revealed low levels of Bnm1 expression in embryogenesis-induced microspores with markedly greater levels of expression in pollen-induced microspores. RNA samples from the globular, heart, torpedo and cotyledonary stages of embryo development did not hybridize with the Bnm1 probe.

EXAMPLE 3

Southern Analysis with the Bnm1 cDNA Probe

Hybridizations for Southern analysis and genomic screening, discussed below, were performed at 42° C. using the following hybridization mixture: 50% formamide, 1× Denhardt's solution (100×: 10 grams of polyvinylpryrrolidone, 10 grams of bovine serum albumin and 10 grams of Ficoll 400 in 500 milliliters of sterile water), 5×SSC buffer (20×: 3M sodium chloride and 0.3M Na₃ Citrate.2H₂O, pH 7.0), 50 mM sodium phosphate (pH 7.0), 1% sodium dodecyl sulfate, and 5 mg/ml heat-denatured salmon sperm DNA. Blots were washed at high stringency (0.1×SSC, 65° C.) and then incubated with X-ray film for various lengths of time to obtain optimum exposure.

In one series of experiments, Bnm1 was probed against a Southern blot of DNA samples obtained from *B. campestris* cv Candle, *B. napus* cv Topas, *B. oleracea* alboglabra, black spruce, *Arabidopsis thaliana*, sunflower, tobacco, barley and corn. The results indicate that the Bnm1 gene is present in black spruce, barley and the crucifers, but not in sunflower, tobacco or corn.

EXAMPLE 4

Isolation of the Bnm1 Genomic Clone

A *Brassica napus* genomic library was constructed partially digesting *B. napus* cv Westar genomic DNA with Sau3A and inserting the DNA fragments (average insert size about 8 kilobases) into the partially gap-filled SalI site of the plasmid pTZ18R. Mead et al., *Protein Eng.* 1: 67 (1986); Nantel et al., *Plant Molecular Biology* 16: 955 (1991). Following the method of Nantel et al., supra, the library was collected in 42 fractions, an aliquot of each fraction was digested with EcoRI, and EcoRI digests were examined by Southern analysis to identify which fraction(s) contained genomic clones corresponding to Bnm1 cDNA.

Approximately 10,000 colonies from each positively hybridizing fraction were screened on Hybond-N filters (Amersham Corp.; Arlington Heights, Ill.) using a $^{32}$P-dCTP random primer labeled cDNA probe. Hybridizing colonies were picked onto duplicate colony grid assay plates for secondary screening. Potential positives were taken through a final, tertiary screen to isolate single positive colonies. After the third round of screening, five clones were identified which showed strong positive signals.

Restriction maps were generated for the five positive genomic clones using the entire Bnm1 cDNA as a probe. The results of these studies suggested that three of the five clones represented the same genomic fragment. One of these three clones plus the remaining two clones (Bnm1-5, 8 and 31) were further characterized. Restriction mapping and Southern analysis eliminated Bnm1-5 as a useful genomic clone.

The lengths of the upstream region in Bnm1-8 and Bnm1-31 were determined by synthesizing the following oligonucleotides to amplify the 5' end of the Bnm1 gene when used in combination with either the universal or reverse sequencing primers:

MSP-1 [SEQ ID NO: 3]:

5' GGCCG<u>AATTC</u>GCCGCCGCGGCGAAGGTAGA 3'
       EcoRI

MSP-2 [SEQ ID NO: 4]:

5' GGCCG<u>AATTC</u>CTGCCTTACCCGTCTCAGCCACG 3'.
       EcoRI

MSP-1 and MSP-2 were designed to generate fragments that differ in size by approximately 230 base pairs. The primers were annealed at 65° C. in 1× polymerase chain reaction (PCR) buffer (Perkin Elmer Corp.; Norwalk, Conn.) containing 2.5 mM MgCl₂.

Two bands, 2.7 kilobases and 3.2 kilobases, were amplified from Bnm1–8 using MSp-1 and MSp-2 primers, respectively, in combination with the reverse sequencing primer. The unexpected 500 base pair difference in size was thought to be due to the presence of an intron. The coding region of the genomic clone was sequenced and the presence of a single, 361 base pair intron was confirmed. FIG. 2 shows the nucleotide sequence [SEQ ID NO: 5] of the Bnm1 genomic clone with upstream and coding regions.

To determine the nucleotide sequences of the PCR fragments, each fragment was digested with EcoRI and a 1.3 kilobase fragment was subcloned into the EcoRI-HincII site of pTZ18R. Ligated DNA molecules were introduced into the *E. coli* strain DH5αMCR-. Subcloned PCR fragments were sequenced using a Sequenase kit (United States Biochemical Corp.; Cleveland, Ohio) which uses the dideoxy-mediated chain termination protocol of Sanger et al., *J. Mol. Biol.* 94: 441 (1975).

The PCR fragments were found to contain only 535 base pairs of the 5' upstream non-translated sequence. A 2.95 kilobase PvuII-BamHI fragment from the original Bnm1 genomic clone was then subcloned to obtain additional upstream sequences. Primer walking was used to sequence a total of 820 bases of the putative promoter region.

EXAMPLE 5

Transformation and Analysis of Canola Transgenics

To examine the function of the Bnm1 promoter, the following set of PCR primers were designed to add a SalI site at the 5' end of the promoter, and to introduce an NcoI site at the ATG codon:

MSP-8 [SEQ ID NO: 6]:

```
           -820
            ◊
5' GGCCGTCGACGCATCAAAGTGATGCGGAAGGAG 3'
      SalI
```

MSP-7 [SEQ ID NO: 7]:

```
                              -1
                               ◊
5' CCCGGGTCTAGAACGTTGCCATGGTCTTTGCGTCG 3'.
         XbaI           NcoI
```

Primer MSP-8 consists of 23 nucleotides of the 5' upstream region starting at nucleotide −820 and also includes an upstream SalI site to facilitate cloning. Primer MSP-7 consists of 23 nucleotides flanking the ATG start codon and was designed to engineer an NcoI site at the start codon of the Bnm1 gene. MSP-7 also includes an XbaI site to facilitate cloning.

Using these primers, an 844 base pair fragment was amplified, cloned and sequenced. The DNA fragment included 820 base pairs of the promoter region directly upstream of the ATG start site of the Bnm1 gene. The nucleotide sequence [SEQ ID NO: 8] of the 844 base pair fragment is shown in FIG. 3.

Figure 5:
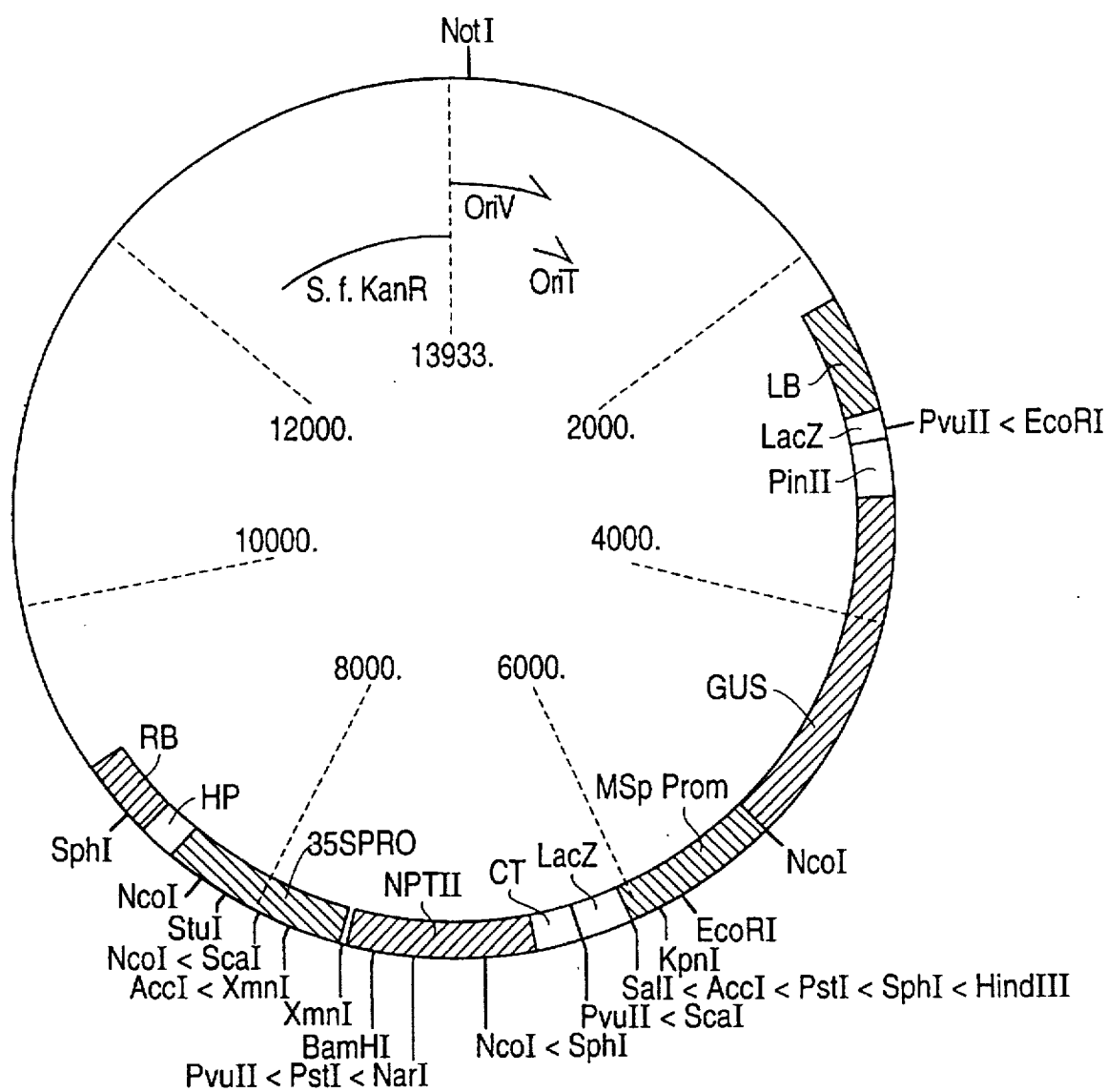
FIG. 5 presents a map of DP5477 which contains the *Brassica napus* microspore promoter (MSp Prom) driving the GUS gene-PINII terminator cassette inserted into the SalI-EcoRI sites of the binary vector DP1741. DP5477 also contains the CaMV 35S promoter driving the neomycin phosphotransferase (NPTII) gene which is used as a selection marker. The left and right T-DNA borders are labeled LB and RB, respectively.

The promoter fragment was digested with NcoI-SalI, ligated to an NcoI-EcoRI fragment containing a GUS reporter gene and the 3' untranslated region (terminator) from a potato proteinase inhibitor (PINII) gene, and cloned into the SalI-EcoRI sites of both pBluescript®II SK+ (Stratagenes Cloning Systems; La Jolla, Calif.) and DP1741 to produce vectors DP5476 (FIG. 4) and DP5477 (FIG. 5), respectively. DP1741 differs from pBI101.1 (Jefferson, *Plant Molecular Biology Reporter* 5: 387 (1987)) by containing CaMV 35S regulatory sequences, rather than nopaline synthase 5' and 3' regulatory sequences, to regulate expression of the NPTII selectable marker gene.

The binary construct DP5477 was transformed into *B. napus* cv Westar via Agrobacterium-mediated co-cultivation of cotyledonary petioles using the general methodology of Moloney et al., *Plant Cell Reports* 8: 238 (1989). Isolated microspores from three out of four canola transgenics analyzed for GUS activity were found to be intensely staining, while the fourth exhibited light blue staining. GUS expression appears to be localized primarily to microspores as other tissues including anther wall, pistil and sepal did not stain. However, the matrix within the locules did stain blue indicating their may be some tapetal expression. Most of the GUS expression appears to be associated with uninucleate and binucleate microspores, and expression is likely to be post-meiotic, because 25 to 50% of the microspores were not stained.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

All publications and patent applications mentioned in this specification are indicative of the level of skill of those in the art to which the invention pertains. All publications and patent applications are herein incorporated by reference to the same extent as if each individual publication or patent application were specifically and individually indicated to be incorporated by reference in its entirety.

---

What is claimed is:

1. A method for producing transgenic plants resistant to virus or insect, comprising:

(a) constructing an expression vector comprising a microspore-specific regulatory element, a promoter, and a foreign gene, wherein said microspore-specific regulatory element comprises SEQ ID NO: 8,
    wherein said microspore-specific regulatory element in conjunction with said promoter control the expression of said foreign gene, and wherein the product of said foreign gene disrupts the function of said virus or encodes an insecticidal toxin, thereby conferring virus or insect resistance.

2. The method of claim 1, wherein said promoter is selected from the group consisting of the Bnm1 promoter, an anther-specific promoter and the CaMV 35S core promoter.

3. The method of claim 2, wherein said promoter is the Bnm1 promoter.

4. The method of claim 1, further comprising the step of:
    (b) introducing said expression vector into embryogenic plant cells.

5. The method of claim 4, wherein said virus-disrupting foreign gene product is selected from the group consisting of viral coat protein, 2'-5' oligoadenylate synthetase, viral genome antisense RNA and pokeweed antiviral protein.

6. The method of claim 5, wherein said viral coat protein is the coat protein of a virus selected from the group consisting of alfalfa mosaic virus, cucumber mosaic virus, tobacco streak virus, potato virus X, potato virus Y, tobacco etch virus, tobacco rattle virus and tobacco mosaic virus.

7. The method of claim 4, wherein said insecticidal toxin is a *Bacillus thuringiensis* endotoxin.

8. The method of claim 7, wherein said *Bacillus thuringiensis* endotoxin is selected from the group consisting of cryIA δ-endotoxin, cryIIIA δ-endotoxin and cryIAc endotoxin.

* * * * *